(12) United States Patent
Bartels et al.

(10) Patent No.: US 10,899,766 B2
(45) Date of Patent: Jan. 26, 2021

(54) BRIDGED PIPERIDINE DERIVATIVES

(71) Applicant: Hoffmann-La Roche Inc., Little Falls, NJ (US)

(72) Inventors: Bjoern Bartels, Basel (CH); Roland Jakob-Roetne, Basel (CH); Anja Limberg, Basel (CH); Werner Neidhart, Basel (CH); Hasane Ratni, Basel (CH); Michael Reutlinger, Basel (CH); Jérôme Charles Sarie, Basel (CH); Greta Vastakaite, Zurich (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/337,348

(22) PCT Filed: Sep. 28, 2017

(86) PCT No.: PCT/EP2017/074575
§ 371 (c)(1),
(2) Date: Mar. 27, 2019

(87) PCT Pub. No.: WO2018/060300
PCT Pub. Date: Apr. 5, 2018

(65) Prior Publication Data
US 2020/0031831 A1    Jan. 30, 2020

(30) Foreign Application Priority Data

Sep. 29, 2016  (EP) .................................. 16191512

(51) Int. Cl.
*C07D 487/04* (2006.01)
*C07D 519/00* (2006.01)
(Continued)

(52) U.S. Cl.
CPC ........ *C07D 487/04* (2013.01); *A61K 31/4196* (2013.01); *A61K 31/55* (2013.01);
(Continued)

(58) Field of Classification Search
CPC .... C07D 487/04; C07D 519/00; A61K 31/55; A61K 31/551; A61K 31/4196; A61P 25/28
(Continued)

(56) References Cited

U.S. PATENT DOCUMENTS 8,703,763 B2 * 4/2014 Baumann ............... A61P 7/04
514/217.04
2020/0031831 A1 * 1/2020 Bartels ................. C07D 519/00

FOREIGN PATENT DOCUMENTS

| CN | 103403003 A | 11/2020 |
| WO | 2011/101304 A2 | 8/2011 |
| WO | 2012/116965 A1 | 9/2012 |

OTHER PUBLICATIONS

Kumar et al. European Journal of Medicinal Chemistry 148 (2018) 436e452.*

(Continued)

*Primary Examiner* — Venkataraman Balasubramanian
(74) *Attorney, Agent, or Firm* — Genentech, Inc.; Richard G. A. Bone

(57) ABSTRACT

The present invention relates to a compound of formula (I), wherein $R^1$ is hydrogen, lower alkyl, lower alkyl substituted by halogen, halogen, lower alkoxy or lower alkoxy substituted by halogen; R may be the same or different, if n=2 or 3; n is 1, 2 or 3; m is 1, 2 or 3; Ar is a five or six membered heteroaryl group, selected from (II), (III), (IV) or (V) wherein $R^2$ is hydrogen, lower alkyl, lower alkyl substituted by halogen, halogen or lower alkoxy; $R^3$ is hydrogen or halogen; -( ) m-is —$(CH_2)_m$— or to pharmaceutically active acid addition salts thereof. The compounds may be used for the treatment of Alzheimer's disease, cerebral amyloid angiopathy, hereditary cerebral hemorrhage with amyloidosis, Dutch-type (HCHWA-D), multi-in-farct dementia, dementia pugilistica or Down syndrome.

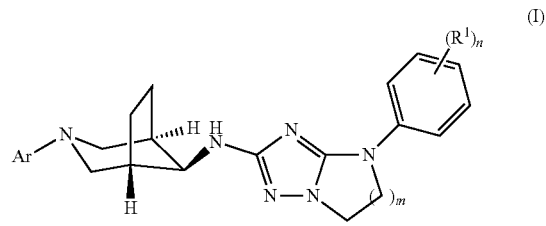

(I)

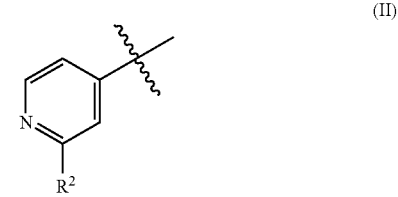

(II)

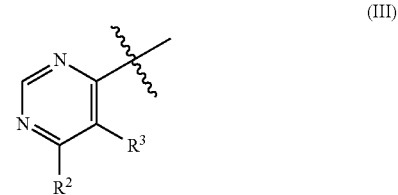

(III)

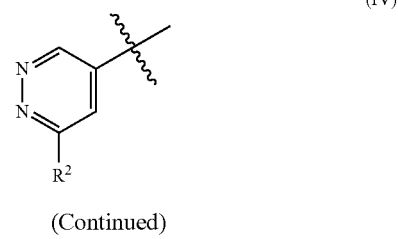

(IV)

(Continued)

-continued

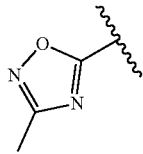

(V)

13 Claims, No Drawings

(51) Int. Cl.
   A61K 31/55      (2006.01)
   A61K 31/4196    (2006.01)
   A61P 25/28      (2006.01)
   A61K 31/551     (2006.01)
(52) U.S. Cl.
   CPC ............ A61K 31/551 (2013.01); A61P 25/28
                   (2018.01); C07D 519/00 (2013.01)
(58) Field of Classification Search
   USPC ...................................... 540/598; 514/217.04
   See application file for complete search history.

(56)         References Cited

OTHER PUBLICATIONS

Bai et al., "An atomic structure of human γ-secretase" Nature 525:212-217 (Sep. 10, 2015).
Beher et al., "Selected Non-steroidal Anti-inflammatory Drugs and Their Derivatives Target g-Secretase at a Novel Site" J Biol Chem 279(42):43519-43426 ( 2004).
Bursavich et al., "Gamma Secretase Modulators: New Alzheimer's Drugs on the Horizon?" Journal of Medicinal Chemistry 59:7389-7409 ( 2016).
Clarke et al., "Intra- or Intercomplex Binding to the g-Secretase Enzyme" Journal of Biological Chemistry 281(42):31279-31289 (Oct. 20, 2006).
Crump et al., "Development and Mechanism of γ-Secretase Modulators for Alzheimer's Disease" Biochemistry 52:3197-3216 ( 2013).
Ebke et al., "Novel g-Secretase Enzyme Modulators Directly Target Presenilin Protein*S" Journal of Biological Chemistry 286(43):37181-37186 (Oct. 28, 2011).
Hall et al., "Y-Secretase Modulators: Current Status and Future Directions" Progress in Medicinal Chemistry 53:101-145 ( 2014).
"International Preliminary Report on Patentability—PCT/EP2017/074575 dated Apr. 11, 2019":108 (dated Apr. 2, 2019).
"International Search Report—PCT/EP2017/074575 dated Oct. 26, 2017":1-12 (dated Oct. 26, 2017).
Jantzen et al., "Microglial Activation and b-Amyloid Deposit Reduction Caused by a Nitric Oxide-Releasing Nonsteroidal Anti-Inflammatory Drug in Amyloid Precursor Protein Plus Presenilin-1 Transgenic Mice" Journal of Neuroscience 22:2246-2254 (Mar. 15, 2002).
Kukar et al., "Diverse compounds mimic Alzheimer disease-causing mutations by augmenting Ab42 production" Nature Medicine 11:545-550 (May 2005).
Lleo et al., "Nonsteroidal anti-inflammatory drugs lower Ab42 and change presenilin 1 conformation" Nature Medicine 10:1065-1066 (Oct. 2004).
Morihara et al., "Selective inhibition of Aβ42 production by NSAID R-enantiomers" Journal of Neurochemistry 83:1009-1012 ( 2002).
Narlawar et al., "Scaffold of the Cyclooxygenase-2 (COX-2) Inhibitor Carprofen Provides Alzheimer G-Secretase Modulators" Journal of Medicinal Chemistry 49:7588-7591 ( 2006).
Oehlrich et al., "γ-Secretase Modulators as Potential Disease Modifying Anti-Alzheimer's Drugs" Journal of Medicinal Chemistry 54:669-698 ( 2011).
Perretto et al., "Synthesis and biological activity of flurbiprofen analogues as elective inhibitors of B-amyloid $_{1-42}$ Secretion" J Med Chem 48:5705-5720 ( 2005).
Stock et al., "The geminal dimethyl analogue of Flurbiprofen as a novel Ab42 inhibitor and potential Alzheimer's disease modifying agent" Bioorganic & Medicinal Chemistry Letters 16:2219-2223 ( 2006).
Takahashi et al., "Sulindac Sulfide Is a Noncompetitive g-Secretase Inhibitor That Preferentially Reduces Ab42 Generation*" Journal of Biological Chemistry 278(20):18664-18670 ( 2003).
Weggen et al., "A subset of NSAIDs lower amyloidogenic Aβ42 independently of cyclooxygenease activity" Nature 414:212-216 (Nov. 8, 2001).

* cited by examiner

BRIDGED PIPERIDINE DERIVATIVES

This application is the National Stage in the United States of International Application No. PCT/EP2017/074575, filed Sep. 28, 2017, which claims benefit of priority to European Patent Application No. 16191512.9 filed Sep. 29, 2016, each of which is incorporated herein by reference in its entirety.

The present invention relates to a compound of formula I,

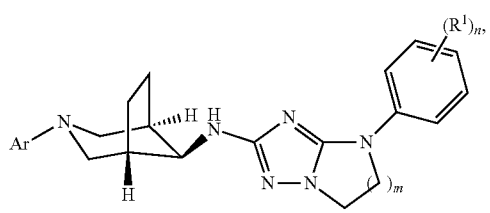

wherein
$R^1$ is hydrogen, lower alkyl, lower alkyl substituted by halogen, halogen, lower alkoxy or lower alkoxy substituted by halogen;
$R^1$ may be the same or different, if n=2 or 3;
n is 1, 2 or 3;
m is 1, 2 or 3;
Ar is a five or six membered heteroaryl group, selected from

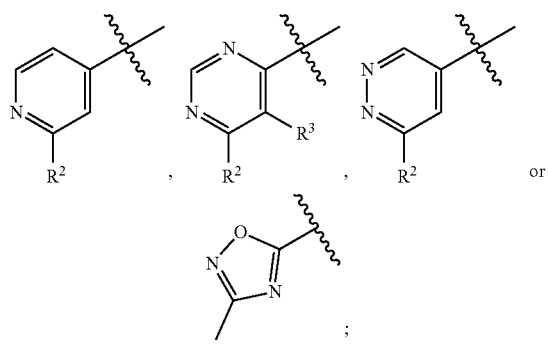

wherein
$R^2$ is hydrogen, lower alkyl, lower alkyl substituted by halogen, halogen or lower alkoxy;
$R^3$ is hydrogen or halogen;
—( )$_m$— is —(CH$_2$)$_m$—
or to pharmaceutically active acid addition salts thereof.

Now it has been found that the present compounds of formula I are modulators of γ-secretase, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP (CTFβ) containing the TM- and cytoplasmatic domain. CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a high molecular weight complex that consists of four essential subunits: Presenilin (PS, including PS1 and PS2), nicastrin, anterior pharynx defective 1 (APH-1), and presenilin enhancer 2 (PEN-2). The atomic structure of human γ-secretase at 3.4 Å resolution has been published (X. Bai, C. Yan, G. Yang, P. Lu, D. Ma, L. Sun, R. Zhou, S. H. W. Scheres, Y. Shi, Nature 2015, 525, pages 212-217. The presenilins are bearing the catalytic site and represent a group of atypical aspartyl proteases which cleave their substrates within the TM of and which are themselves polytopic membrane proteins. The other essential components of γ-secretase, nicastrin and the products of the aph1 and pen-2 genes are believed to be responsible for substrate recognition and recruitment. Proven substrates for γ-secretase are APP and the proteins of the Notch receptor family, however, γ-secretase has a loose substrate specificity and many further membrane proteins unrelated to APP and Notch have been reported to be cleaved by the γ-secretase in vitro.

The γ-secretase activity is absolutely required for the production of Aβ peptides. This has been shown both by genetic means, i.e., ablation of the presenilin genes and by low-molecular-weight inhibitory compounds. According to the amyloid cascade hypothesis for AD the production and deposition of Aβ is the ultimate cause for the disease. Therefore, it was believed that selective and potent inhibition of γ-secretase might be useful for the prevention and treatment of AD.

An alternative mode of treatment is the modulation of the γ-secretase activity which results in a selective reduction of the Aβ42 production. This will lead in an increase of shorter Aβ isoforms, such as Aβ38, Aβ37 or others, which have no or reduced capability for aggregation and plaque formation, and are not or less neurotoxic. Compounds which show this effect on modulating y-secretase activity include certain non-steroidal anti-inflammatory drugs (NSAIDs) and related analogues (Weggen et al., Nature, 414 (2001) 212-16).

Thus, the compounds of this invention will be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Numerous documents describe the current knowledge on y-secretase modulation, for example the following publications:

Morihara et al, J. Neurochem., 83 (2002) 1009-12
Jantzen et al, J.Neuroscience, 22 (2002) 226-54

Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91
Ebke et al, J. Biol. Chem., 286 (2011) 37181-86
Oehlich, Gijsen et al, J. Med. Chem., 54 (2011), 669-698
Li et al., Biochemistry, 52, (2013), 3197-3216
Hall et al, Progress in Med. Chem., 53 (2014) 101-145
Bursavich et al, J. Med. Chem., 59 (2016) DOI: 10.1021/acs.jmedchem.5b01960

The following definitions for compounds of formula I are used:

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkyl substituted by halogen" denotes an alkyl group as defined above, wherein at least one hydrogen atom is replaced by halogen, for example $CF_3$, $CHF_2$, $CH_2F$, $CHFCF_3$, $CH_2CHF_2$, $CH_2CH_2F$, $CH_2C(CH_3)_2CF_3$, $CH_2CF_2CF_3$, $CH(CF_3)_2$, $CH_2CF_3$, $(CH_2)_2CF_3$, $(CH_2)_3CF_3$, $CH(CH_3)CF_3$, $CF_2CF_3$, and the like. The preferred group is $CF_3$.

The term "lower alkoxy" denotes a lower alkyl group as defined above, which group is connected via an O atom.

The term "lower alkoxy substituted by halogen" denotes a lower alkoxy group as defined above, wherein at least one hydrogen atom is replaced by halogen.

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Objects of the present invention are compounds of formula I, the use of such compounds for the preparation of medicaments for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome, their manufacture and medicaments based on a compound of formula I in accordance with the invention.

Further objects of the present invention are all forms of optically pure enantiomers, racemates or diastereometric mixtures for compounds of formula I.

One object of the present invention is a compound of formula I-1,

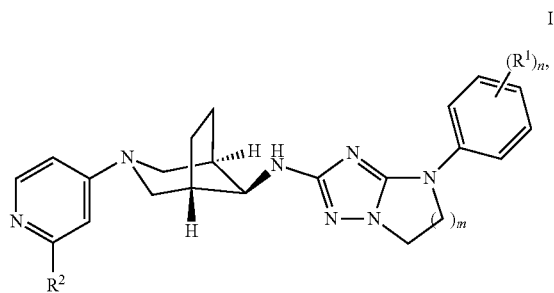

I-1 wherein $R^1$ is hydrogen, lower alkyl, lower alkyl substituted by halogen, halogen, lower alkoxy or lower alkoxy substituted by halogen;

$R^1$ may be the same or different, if n=2 or 3;

n is 1, 2 or 3;

m is 1, 2 or 3;

$R^2$ is hydrogen, lower alkyl, lower alkyl substituted by halogen, halogen or lower alkoxy;

-( )$_m$- is —$(CH_2)_m$— or a pharmaceutically active acid addition salts thereof, for example the following compounds 4-(3,4-difluorophenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine N-[(1R,5S,8S)-3-(2-chloro-4-pyridyl)-3-azabicyclo[3.2.1]octan-8-yl]-4-(3,4-difluorophenyl)-6,7-dihydro-5H-[1,2,4]triazolo[1,5-a]pyrimidin-2-amine 4-(3,4-difluorophenyl)-N-[(1R,5S,8S)-3-[2-(trifluoromethyl)-4-pyridyl]-3-azabicyclo[3.2.1]octan-8-yl]-5,6-dihydroimidazo[1,2-b][1,2,4]triazol-2-amine 4-[4-(trifluoromethyl)phenyl]-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine 4-[4-(trifluoromethyl)phenyl]-N-[(1R,5S,8S)-3-[2-(trifluoromethyl)-4-pyridyl]-3-azabicyclo[3.2.1]octan-8-yl]-5,6,7,8-tetrahydro-[1,2,4]triazolo[1,5-a][1,3]diazepin-2-amine 4-(3-fluoro-4-methyl-phenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine 4-(3,4-difluorophenyl)-N-[(1R,5S,8S)-3-(2-methoxy-4-pyridyl)-3-azabicyclo[3.2.1]octan-8-yl]-6,7-dihydro-5H-[1,2,4]triazolo[1,5-a]pyrimidin-2-amine 4-(3,4-difluorophenyl)-N-[(1R,5S,8S)-3-[2-(trifluoromethyl)-4-pyridyl]-3-azabicyclo[3.2.1]octan-8-yl]-5,6,7,8-tetrahydro-[1,2,4]triazolo[1,5-a][1,3]diazepin-2-amine N-[(1R,5S,8S)-3-[2-(trifluoromethyl)-4-pyridyl]-3-azabicyclo[3.2.1]octan-8-yl]-4-(2,3,4-trifluorophenyl)-6,7-dihydro-5H-[1,2,4]triazolo[1,5-a]pyrimidin-2-amine 4-(3-fluorophenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine 4-(4-fluorophenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine 4-(4-fluorophenyl)-N-[(1R,5S,8S)-3-(2-methoxy-4-pyridyl)-3-azabicyclo[3.2.1]octan-8-yl]-6,7-dihydro-5H-[1,2,4]triazolo[1,5-a]pyrimidin-2-amine 4-(3,5-difluorophenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine 4-(3-fluorophenyl)-N-[(1R,5S,8S)-3-(2-methoxy-4-pyridyl)-3-azabicyclo[3.2.1]octan-8-yl]-6,7-dihydro-5H-[1,2,4]triazolo[1,5-a]pyrimidin-2-amine 4-(3,5-difluorophenyl)-N-[(1R,5S,8S)-3-(2-methoxy-4-pyridyl)-3-azabicyclo[3.2.1]octan-8-yl]-6,7-dihydro-5H-[1,2,4]triazolo[1,5-a]pyrimidin-2-amine or 4-(4-methoxyphenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine.

One further object of the present invention is a compound of formula I-2,

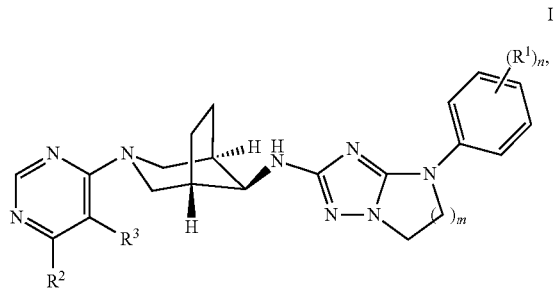

I-2 wherein
R¹ is hydrogen, lower alkyl, lower alkyl substituted by halogen, halogen, lower alkoxy or lower alkoxy substituted by halogen;
R¹ may be the same or different, if n=2 or 3;
n is 1, 2 or 3;
m is 1, 2 or 3;
R² is hydrogen, lower alkyl, lower alkyl substituted by halogen, halogen or lower alkoxy;
R³ is hydrogen or halogen;
-( )$_m$- is —(CH$_2$)$_m$—
or a pharmaceutically active acid addition salts thereof, for example the following compounds 4-(3,4-difluorophenyl)-N-[(1R,5S,8S)-3-(6-methylpyrimidin-4-yl)-3-azabicyclo[3.2.1]octan-8-yl]-6,7-dihydro-5H-[1,2,4]triazolo[1,5-a]pyrimidin-2-amine 4-(3,4-difluorophenyl)-N-[(1R,5S,8S)-3-(6-methylpyrimidin-4-yl)-3-azabicyclo[3.2.1]octan-8-yl]-5,6-dihydroimidazo[1,2-b][1,2,4]triazol-2-amine N-[(1R,5S,8S)-3-(6-methylpyrimidin-4-yl)-3-azabicyclo[3.2.1]octan-8-yl]-4-[4-(trifluoromethyl)phenyl]-6,7-dihydro-5H-[1,2,4]triazolo[1,5-a]pyrimidin-2-amine N-[(1R,5S,8S)-3-(6-methylpyrimidin-4-yl)-3-azabicyclo[3.2.1]octan-8-yl]-4-[4-(trifluoromethyl)phenyl]-5,6,7,8-tetrahydro-[1,2,4]triazolo[1,5-a][1,3]diazepin-2-amine 4-(3-fluoro-4-methyl-phenyl)-N-[(1R,5S,8S)-3-(6-methylpyrimidin-4-yl)-3-azabicyclo[3.2.1]octan-8-yl]-6,7-dihydro-5H-[1,2,4]triazolo[1,5-a]pyrimidin-2-amine N-[(1R,5S,8S)-3-(6-methylpyrimidin-4-yl)-3-azabicyclo[3.2.1]octan-8-yl]-4-[4-(trifluoromethyl)phenyl]-5,6-dihydroimidazo[1,2-b][1,2,4]triazol-2-amine N-[(1R,5S,8S)-3-(6-chloropyrimidin-4-yl)-3-azabicyclo[3.2.1]octan-8-yl]-4-(3-fluoro-4-methyl-phenyl)-6,7-dihydro-5H-[1,2,4]triazolo[1,5-a]pyrimidin-2-amine 4-(3,4-difluorophenyl)-N-[(1R,5S,8S)-3-(6-methoxypyrimidin-4-yl)-3-azabicyclo[3.2.1]octan-8-yl]-6,7-dihydro-5H-[1,2,4]triazolo[1,5-a]pyrimidin-2-amine N-[(1R,5S,8S)-3-(6-chloropyrimidin-4-yl)-3-azabicyclo[3.2.1]octan-8-yl]-4-(3,4-difluorophenyl)-6,7-dihydro-5H-[1,2,4]triazolo[1,5-a]pyrimidin-2-amine 4-(3,4-difluorophenyl)-N-[(1R,5S,8S)-3-(5-fluoro-6-methyl-pyrimidin-4-yl)-3-azabicyclo[3.2.1]octan-8-yl]-6,7-dihydro-5H-[1,2,4]triazolo[1,5-a]pyrimidin-2-amine 4-(3,4-difluorophenyl)-N-[(1R,5S,8S)-3-(6-methylpyrimidin-4-yl)-3-azabicyclo[3.2.1]octan-8-yl]-5,6,7,8-tetrahydro-[1,2,4]triazolo[1,5-a][1,3]diazepin-2-amine 4-(3,4-difluorophenyl)-N-[(1R,5S,8S)-3-(6-methoxypyrimidin-4-yl)-3-azabicyclo[3.2.1]octan-8-yl]-5,6,7,8-tetrahydro-[1,2,4]triazolo[1,5-a][1,3]diazepin-2-amine N-[(1R,5S,8S)-3-(6-methylpyrimidin-4-yl)-3-azabicyclo[3.2.1]octan-8-yl]-4-(2,3,4-trifluorophenyl)-6,7-dihydro-5H-[1,2,4]triazolo[1,5-a]pyrimidin-2-amine N-[(1R,5S,8S)-3-(6-methoxypyrimidin-4-yl)-3-azabicyclo[3.2.1]octan-8-yl]-4-(2,3,4-trifluorophenyl)-6,7-dihydro-5H-[1,2,4]triazolo[1,5-a]pyrimidin-2-amine 4-(3-fluorophenyl)-N-[(1R,5S,8S)-3-(6-methylpyrimidin-4-yl)-3-azabicyclo[3.2.1]octan-8-yl]-6,7-dihydro-5H-[1,2,4]triazolo[1,5-a]pyrimidin-2-amine 4-(4-fluorophenyl)-N-[(1R,5S,8S)-3-(6-methylpyrimidin-4-yl)-3-azabicyclo[3.2.1]octan-8-yl]-6,7-dihydro-5H-[1,2,4]triazolo[1,5-a]pyrimidin-2-amine 4-(4-fluorophenyl)-N-[(1R,5S,8S)-3-(6-methoxypyrimidin-4-yl)-3-azabicyclo[3.2.1]octan-8-yl]-6,7-dihydro-5H-[1,2,4]triazolo[1,5-a]pyrimidin-2-amine 4-(3,5-difluorophenyl)-N-[(1R,5S,8S)-3-(6-methylpyrimidin-4-yl)-3-azabicyclo[3.2.1]octan-8-yl]-6,7-dihydro-5H-[1,2,4]triazolo[1,5-a]pyrimidin-2-amine N-[(1R,5S,8S)-3-(5-fluoro-6-methyl-pyrimidin-4-yl)-3-azabicyclo[3.2.1]octan-8-yl]-4-(4-fluorophenyl)-6,7-dihydro-5H-[1,2,4]triazolo[1,5-a]pyrimidin-2-amine N-[(1R,5S,8S)-3-(5-fluoro-6-methyl-pyrimidin-4-yl)-3-azabicyclo[3.2.1]octan-8-yl]-4-(3-fluorophenyl)-6,7-dihydro-5H-[1,2,4]triazolo[1,5-a]pyrimidin-2-amine 4-(3-fluorophenyl)-N-[(1R,5S,8S)-3-(6-methoxypyrimidin-4-yl)-3-azabicyclo[3.2.1]octan-8-yl]-6,7-dihydro-5H-[1,2,4]triazolo[1,5-a]pyrimidin-2-amine or N-[(1R,5S,8S)-3-(6-methylpyrimidin-4-yl)-3-azabicyclo[3.2.1]octan-8-yl]-4-(2,3,4-trifluorophenyl)-5,6-dihydroimidazo[1,2-b][1,2,4]triazol-2-amine.

One object of the present invention is a compound of formula I-3,

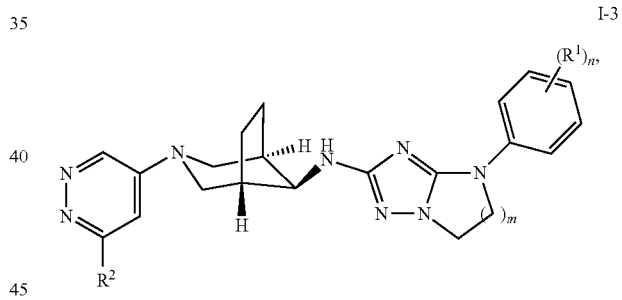

I-3 wherein
R¹ is hydrogen, lower alkyl, lower alkyl substituted by halogen, halogen, lower alkoxy or lower alkoxy substituted by halogen;
R¹ may be the same or different, if n=2 or 3;
n is 1, 2 or 3;
m is 1, 2 or 3;
R² is hydrogen, lower alkyl, lower alkyl substituted by halogen, halogen or lower alkoxy;
-( )$_m$- is —(CH$_2$)$_m$—
or a pharmaceutically active acid addition salts thereof, for example the following compounds N-[(1R,5S,8S)-3-(6-chloropyridazin-4-yl)-3-azabicyclo[3.2.1]octan-8-yl]-4-(3,4-difluorophenyl)-6,7-dihydro-5H-[1,2,4]triazolo[1,5-a]pyrimidin-2-amine 4-(3,4-difluorophenyl)-N-[(1R,5S,8S)-3-(6-methoxypyridazin-4-yl)-3-azabicyclo[3.2.1]octan-8-yl]-6,7-dihydro-5H-[1,2,4]triazolo[1,5-a]pyrimidin-2-amine 4-(3,4-difluorophenyl)-N-[(1R,5S,8S)-3-(6-methylpyridazin-4-yl)-3-azabicyclo[3.2.1]octan-8-yl]-6,7-dihydro-5H-[1,2,4]triazolo[1,5-a]pyrimidin-2-amine N-[(1R,5S,8S)-3-(6-chloropyridazin-4-yl)-3-azabicyclo[3.2.1]octan-8-yl]-4-(3,4-difluorophenyl)-5,6,7,8-tetrahydro-[1,2,4]triazolo[1,5-a][1,3]diazepin-2-amine
4-(3,4-difluorophenyl)-N-[(1R,5S,8S)-3-(6-methoxypyridazin-4-yl)-3-azabicyclo[3.2.1]octan-8-yl]-5,6,7,8-tetrahydro-[1,2,4]triazolo[1,5-a][1,3]diazepin-2-amine
4-(3,4-difluorophenyl)-N-[(1R,5S,8S)-3-(6-methylpyridazin-4-yl)-3-azabicyclo[3.2.1]octan-8-yl]-5,6,7,8-tetrahydro-[1,2,4]triazolo[1,5-a][1,3]diazepin-2-amine
N-[(1R,5S,8S)-3-(6-chloropyridazin-4-yl)-3-azabicyclo[3.2.1]octan-8-yl]-4-(2,3,4-trifluorophenyl)-6,7-dihydro-5H-[1,2,4]triazolo[1,5-a]pyrimidin-2-amine
N-[(1R,5S,8S)-3-(6-methoxypyridazin-4-yl)-3-azabicyclo[3.2.1]octan-8-yl]-4-(2,3,4-trifluorophenyl)-6,7-dihydro-5H-[1,2,4]triazolo[1,5-a]pyrimidin-2-amine
4-(4-fluorophenyl)-N-[(1R,5S,8S)-3-(6-methoxypyridazin-4-yl)-3-azabicyclo[3.2.1]octan-8-yl]-6,7-dihydro-5H-[1,2,4]triazolo[1,5-a]pyrimidin-2-amine or
4-(3-fluorophenyl)-N-[(1R,5S,8S)-3-(6-methoxypyridazin-4-yl)-3-azabicyclo[3.2.1]octan-8-yl]-6,7-dihydro-5H-[1,2,4]triazolo[1,5-a]pyrimidin-2-amine.

One object of the present invention is a compound of formula I-4,

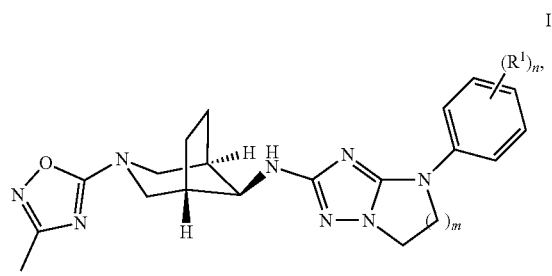

I-4 wherein
R$^1$ is hydrogen, lower alkyl, lower alkyl substituted by halogen, halogen, lower alkoxy or lower alkoxy substituted by halogen;
R$^1$ may be the same or different, if n=2 or 3;
n is 1, 2 or 3;
m is 1, 2 or 3;
-( )$_m$- is —(CH$_2$)$_m$—
or a pharmaceutically active acid addition salts thereof, for example the following compounds
4-(3,4-difluorophenyl)-N-[(1R,5S,8S)-3-(3-methyl-1,2,4-oxadiazol-5-yl)-3-azabicyclo[3.2.1]octan-8-yl]-6,7-dihydro-5H-[1,2,4]triazolo[1,5-a]pyrimidin-2-amine or
4-(3,4-difluorophenyl)-N-[(1R,5S,8S)-3-(3-methyl-1,2,4-oxadiazol-5-yl)-3-azabicyclo[3.2.1]octan-8-yl]-5,6,7,8-tetrahydro-[1,2,4]triazolo[1,5-a][1,3]diazepin-2-amine.

Further objects of the present invention are compounds of formulas

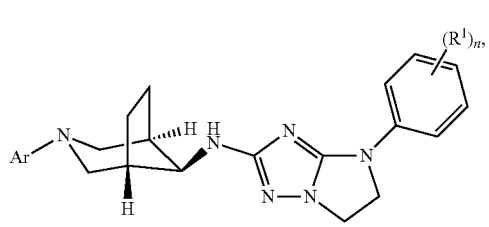

Ia

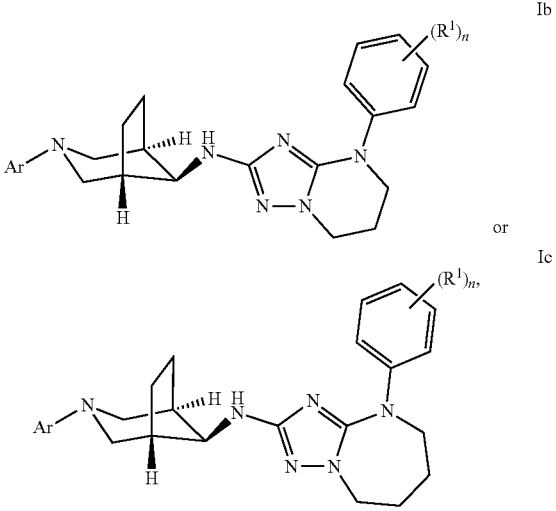

Ib or

Ic wherein
R$^1$ is hydrogen, lower alkyl, lower alkyl substituted by halogen, halogen, lower alkoxy or lower alkoxy substituted by halogen;
R$^1$ may be the same or different, if n=2 or 3;
n is 1, 2 or 3;
Ar is a five or six membered heteroaryl group, selected from

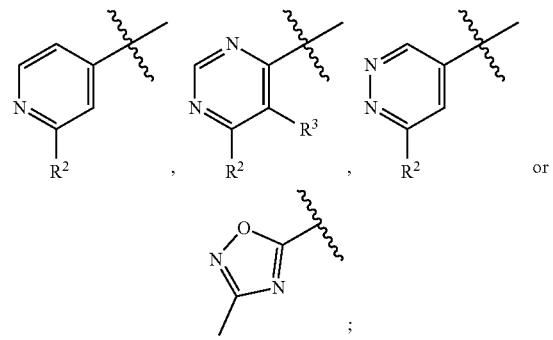

wherein
R$^2$ is hydrogen, lower alkyl, lower alkyl substituted by halogen, halogen or lower alkoxy;
R$^3$ is hydrogen or halogen;
or pharmaceutically active acid addition salts thereof.

The present compounds of formula I and their pharmaceutically acceptable salts can be prepared by methods known in the art, for example, by processes described below, which processes comprise
a) reacting a compound of formula 9

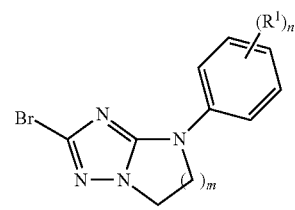

with a compound of formula 10

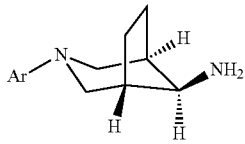

to a compound of formula I

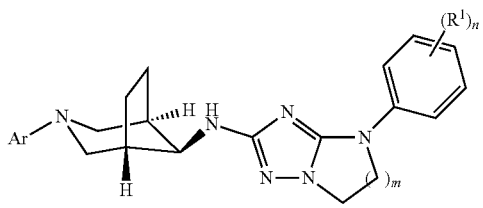

wherein the substituents have the meaning as described above, and, if desired, converting the compounds obtained into pharmaceutically acceptable acid addition salts;

In more detail, compounds of formula I and their intermediates may be prepared by schemes 1-4 and by the description of 50 specific examples.

General Synthesis Schemes

General Synthesis of Derivatives of Type Ia with $m=1$

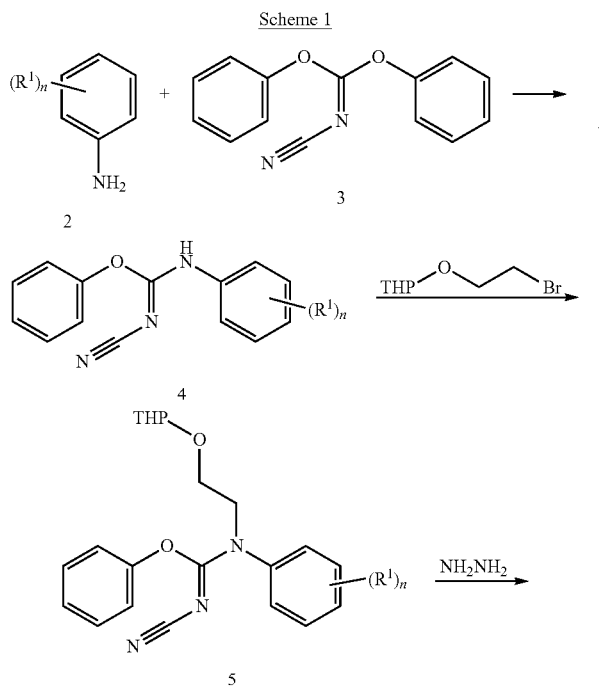

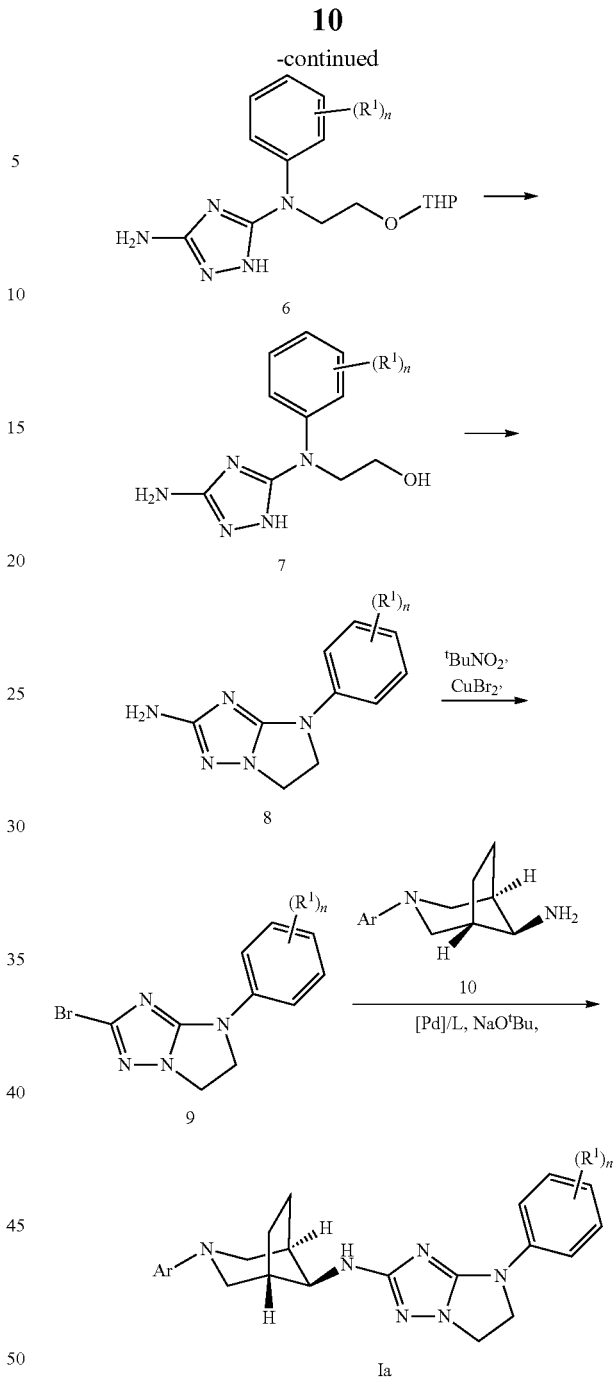

The preparation of derivatives of general formula Ia with ($m=1$), where made according to the scheme 1. The synthesis of target compounds commenced by the nucleophilic addition of a commercially available substituted anilines 2 onto the diphenyl cyanocarbonimidate 3 leading to the intermediates 4 in a good yield. Upon N-alkylation with an electrophile [2-(2-bromoethoxy)tetrahydropyran] containing a protected alcohol moiety the compounds 5 were obtained. Upon reaction with hydrazine the corresponding triazoles 6 were obtained. Deprotection of the alcohol protected by tetrahydropyran (THP) group under standard acidic conditions afforded 7 in nearly quantitative yield, the alcohol precursor for the Mitsunobu reaction forming 8. Finally, a Sandmeyer reaction led to the versatiles intermediates bromotriazole 9, which can easily undergo a Buchwald type reaction with different amines of type 10 affording final products of formula Ia.

General Synthesis of Derivatives of Type Ib with m=2

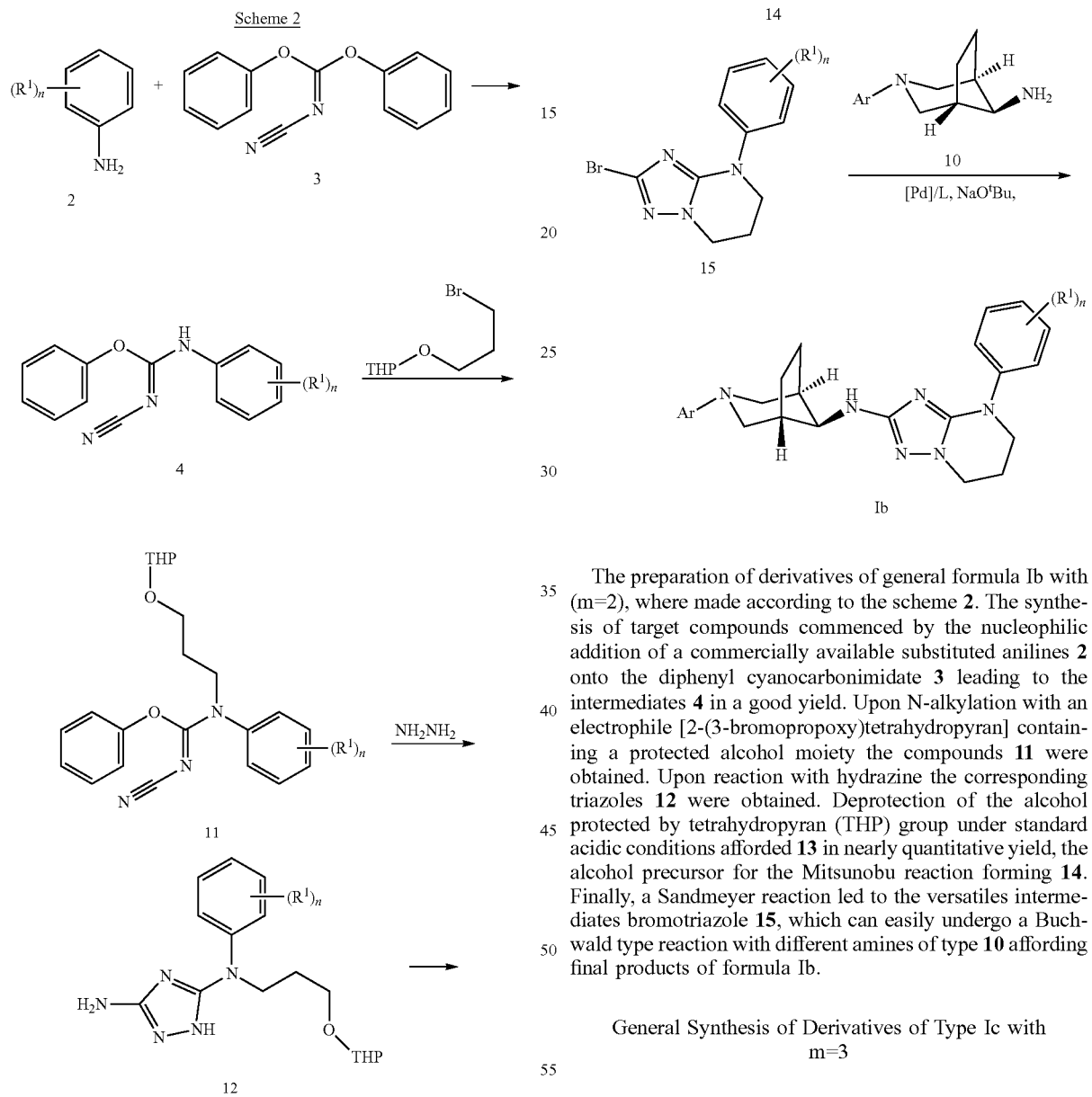

The preparation of derivatives of general formula Ib with (m=2), where made according to the scheme 2. The synthesis of target compounds commenced by the nucleophilic addition of a commercially available substituted anilines 2 onto the diphenyl cyanocarbonimidate 3 leading to the intermediates 4 in a good yield. Upon N-alkylation with an electrophile [2-(3-bromopropoxy)tetrahydropyran] containing a protected alcohol moiety the compounds 11 were obtained. Upon reaction with hydrazine the corresponding triazoles 12 were obtained. Deprotection of the alcohol protected by tetrahydropyran (THP) group under standard acidic conditions afforded 13 in nearly quantitative yield, the alcohol precursor for the Mitsunobu reaction forming 14. Finally, a Sandmeyer reaction led to the versatiles intermediates bromotriazole 15, which can easily undergo a Buchwald type reaction with different amines of type 10 affording final products of formula Ib.

General Synthesis of Derivatives of Type Ic with m=3

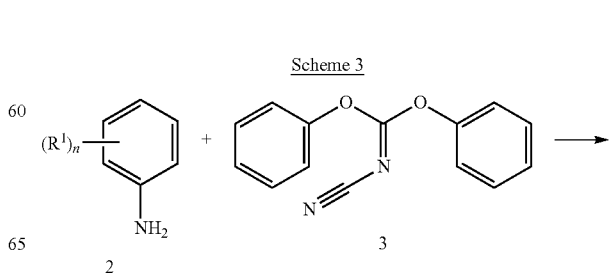

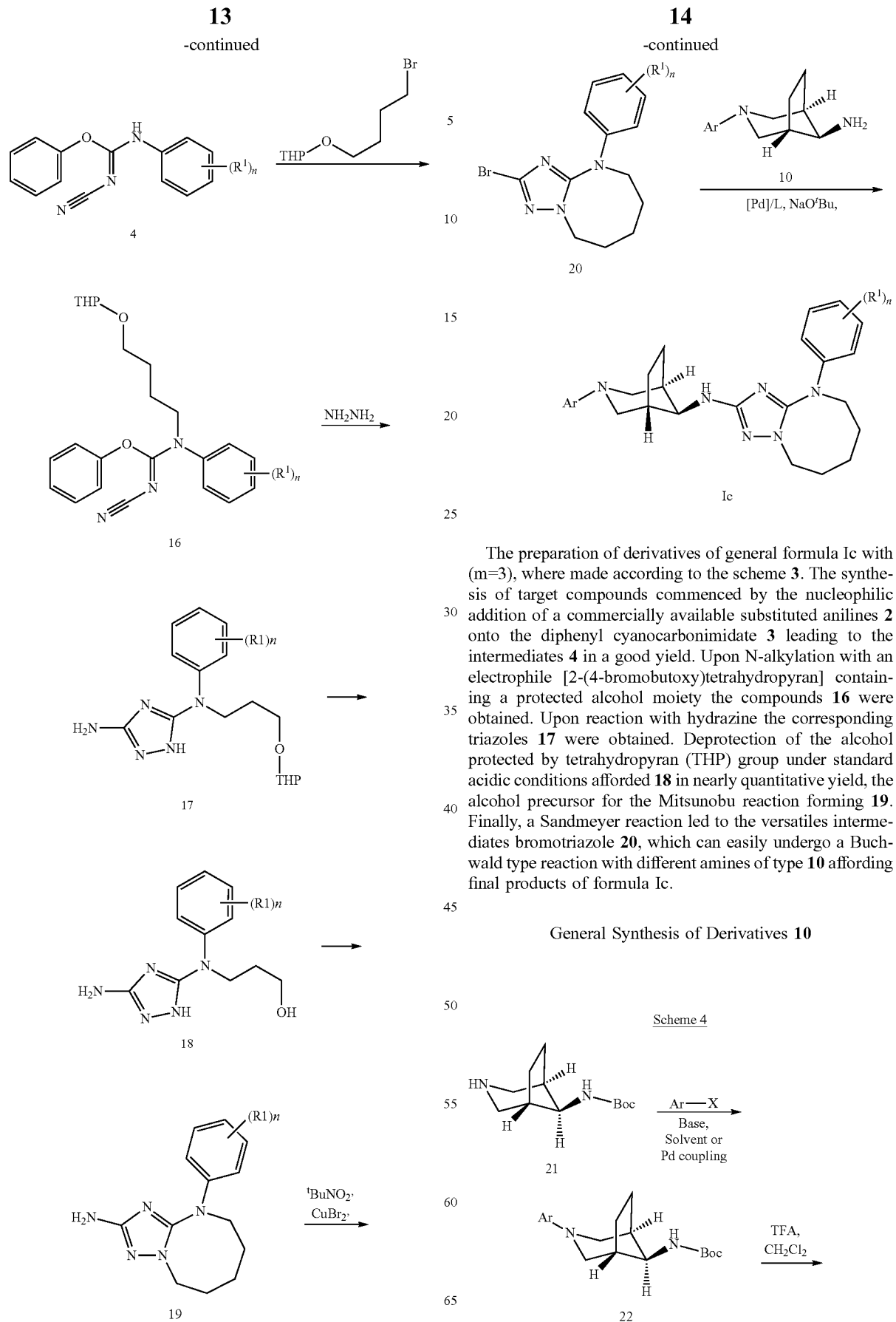

The preparation of derivatives of general formula Ic with (m=3), where made according to the scheme 3. The synthesis of target compounds commenced by the nucleophilic addition of a commercially available substituted anilines 2 onto the diphenyl cyanocarbonimidate 3 leading to the intermediates 4 in a good yield. Upon N-alkylation with an electrophile [2-(4-bromobutoxy)tetrahydropyran] containing a protected alcohol moiety the compounds 16 were obtained. Upon reaction with hydrazine the corresponding triazoles 17 were obtained. Deprotection of the alcohol protected by tetrahydropyran (THP) group under standard acidic conditions afforded 18 in nearly quantitative yield, the alcohol precursor for the Mitsunobu reaction forming 19. Finally, a Sandmeyer reaction led to the versatiles intermediates bromotriazole 20, which can easily undergo a Buchwald type reaction with different amines of type 10 affording final products of formula Ic.

General Synthesis of Derivatives 10

Scheme 4

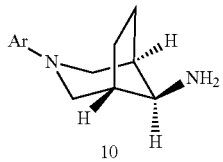

Compounds of formula 10 used in schemes 1-3 can be prepared according to the scheme 4, can be synthesized starting from tert-butyl N-[(1S,5R,8S)-3-azabicyclo[3.2.1]octan-8-yl]carbamate 21 (CAS 847862-26-4). The coupling of 21 with heterocyclic halides of general formula Ar—X can be accomplished under thermal conditions in a solvent such as ethanol or NMP in the presence of a base such as $Et_3N$ or by using displacement reactions under catalytic conditions (like e.g. palladium(0) or copper(II) catalysis) to provide compounds of formula 22. After deprotection with acid e.g. trifluoro acetic acid compounds of formula 10 were obtained.

The heterocycles halides are either commercial available, known in the literature so they can be prepared by methods known in the art or alternatively could be prepared as described in the specification.

The compounds were investigated in accordance with the test given hereinafter.

DESCRIPTION OF γ-SECRETASE ASSAY

Cellular γ-Secretase Assay

Human neuroglioma H4 cells overexpressing human APP695 with the Swedish double mutation (K595N/M596L) were plated at 30,000 cells/well/100 µl in 96-well plates in IMDM media containing 10% FCS, 0.2 mg/l Hygromycin B and incubated at 37° C., 5% $CO_2$.

3-4 hr post plating, compounds are a diluted in media and 50 µl is added as 1.5-fold concentrate to achieve the final concentration. Compound incubation is performed for 24 hr. Final doses typically range from 4 µM down to 0.0013 µM in half-log steps resulting in a eight point dose response curve.

Appropriate controls using vehicle only and reference compound were applied to this assay. The final concentration of $Me_2SO$ was 0.4%.

After incubation at 37° C., 5% $CO_2$, the supernatant was subjected to quantification of secreted Aβ42 by the means of an AlphaLisa assay kit (Human Amyloid beta 1-42 Kit: Cat # AL203C, Perkin Elmer). 20 µl of the cell culture supernatant was transferred to an assay plate. Then 10 µl of a mixture of the AlphaLisa coupled capture antibody and the biotinylated detection antibody was added and incubated for 3 hours at room temperature while softly shaking the assay plate. After a further addition of 20 µl of the Donor beads the assay plate was incubated for 30 min at room temperature and constant shaking without exposure to direct light.

The assay plate was then read on a Paradigm AlphaLisa Reader using the build-in program with excitation at 680 nm and emission at 570 nm.

The measured signals were then used to calculate $IC_{50}$ values for inhibition of Aβ42 secretion by nonlinear regression fit analysis using XLfit 5.3 software (IDBS).

The table below shows the data for all compounds for the inhibition of Aβ42 secretion (nM):

| Example No. | $EC_{50}$ Aβ42 (uM) | Example No. | $EC_{50}$ Aβ42 (nM) |
|---|---|---|---|
| 1 | 0.0158 | 26 | 0.0463 |
| 2 | 0.0059 | 27 | 0.0378 |
| 3 | 0.0264 | 28 | 0.0593 |
| 4 | 0.0892 | 29 | 0.0233 |
| 5 | 0.0356 | 30 | 0.0320 |
| 6 | 0.0214 | 31 | 0.0294 |
| 7 | 0.0302 | 32 | 0.0277 |
| 8 | 0.0117 | 33 | 0.0404 |
| 9 | 0.0192 | 34 | 0.0144 |
| 10 | 0.0312 | 35 | 0.0306 |
| 11 | 0.0278 | 36 | 0.0232 |
| 12 | 0.0268 | 37 | 0.0344 |
| 13 | 0.0114 | 38 | 0.0402 |
| 14 | 0.0155 | 39 | 0.0141 |
| 15 | 0.0306 | 40 | 0.0092 |
| 16 | 0.0172 | 41 | 0.0158 |
| 17 | 0.0580 | 42 | 0.0406 |
| 18 | 0.0264 | 43 | 0.0259 |
| 19 | 0.0139 | 44 | 0.0308 |
| 20 | 0.0231 | 45 | 0.0130 |
| 21 | 0.0147 | 46 | 0.0103 |
| 22 | 0.0348 | 47 | 0.0234 |
| 23 | 0.0233 | 48 | 0.0264 |
| 24 | 0.0804 | 49 | 0.0064 |
| 25 | 0.0234 | 50 | 0.0570 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions. The administration can also be effected topically, e.g. transdermal administration, or in form of eye drops or ear drops.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

|  |  | mg/tablet | | | |
| --- | --- | --- | --- | --- | --- |
| Item | Ingredients | 5 | 25 | 100 | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
|  | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

|  |  | mg/capsule | | | |
| --- | --- | --- | --- | --- | --- |
| Item | Ingredients | 5 | 25 | 100 | 500 |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
|  | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Experimental Part

The following examples are provided for illustration of the invention. They should not be considered as limiting the scope of the invention, but merely as being representative thereof.

General

Analytical Methods

HPLC (method LCMS_fastgradient)

Column: Agilent Zorbax Eclipse Plus C18, Rapid Resolution HT, 2.1×30 mm, 1.8 μm, Part.no. 959731-902

Solvent A: Water 0.01% Formic Acid; Solvent B: acetonitrile (MeCN)

Gradients:

| Time [min] | Flow Rate [ml/min] | % A | % B |
| --- | --- | --- | --- |
| Initial | 0.8 | 97 | 3 |
| 0.2 | 1.0 | 97 | 3 |
| 1.7 | 1.0 | 3 | 97 |
| 2.0 | 1.0 | 3 | 97 |
| 2.1 | 1.0 | 97 | 3 |

Abbreviations

The following abbreviations were used in the experimental part:
THF=tetrahydrofurane;
TBME=methyl-tert-butylether;
DMF=dimethylformamide;
TLC=thin layer chromatography;
RT=room temperature, 20-25° C.

Preparation of Intermediates

Intermediates of type 9 (according to scheme 1)

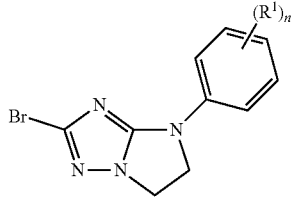

Intermediate 9-1:

2-bromo-4-(3,4-difluorophenyl)-5,6-dihydroimidazo[1,2-b][1,2,4]triazole

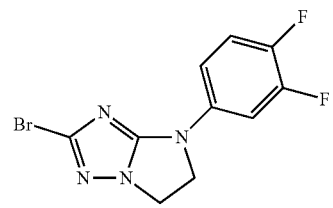

9-1

Step 1: 3,4-Difluoroaniline (3.00 g, 23.20 mmol) and diphenyl cyanocarbonimidate (5.53 g, 23.20 mmol) were dissolved in 2-propanol (64.00 mL). The reaction mixture was stirred at RT overnight. The crude was evaporated in vacuo and purified by column chromatography (Hept:EtOAc 100:0 to 50:50) to afford (Z)-phenyl N'-cyano-N-(3,4-difluorophenyl) carbamimidate as a white solid (5.00 g, 79%). MS (ES+) m/z: 274.1 [M+H]⁺.

Step 2: A solution of 2-(2-bromoethoxy)tetrahydro-2H-pyran (5.74 g, 4.15 mL, 27.40 mmol), (Z)-phenyl N'-cyano-N-(3,4-difluorophenyl)carbamimidate (5.00 g, 18.30 mmol) and K₂CO₃ (5.06 g, 36.60 mmol) in DMF (180 mL) was heated at 85° C. overnight. An extra amount of 2-(2-bromoethoxy)tetrahydro-2H-pyran (5.74 g, 4.15 mL, 27.40 mmol) and K₂CO₃ (5.06 g, 36.60 mmol) were added and the reaction stirred at 100° C. for a further 8 hours and then at 75° C. overnight. The reaction mixture was cooled down to RT, poured onto a saturated aqueous solution of NH₄Cl and the product extracted three times with EtOAc. The organic layers were combined, washed with water and then with brine, dried over sodium sulfate, filtered and evaporated in vacuo. The residue was then purified by column chromatography using (Hept:EtOAc 100:0 to 70:30) to afford (Z)-phenyl N'-cyano-N-(3,4-difluorophenyl)-N-(2-((tetrahydro-2H-pyran-2-yl)oxy)ethyl)carbamimidate as a yellow oil (1.75 g, 24%). MS (ES+) m/z: 402.2 [M+H]$^+$.

Step 3: To a solution of (Z)-Phenyl N'-cyano-N-(3,4-difluorophenyl)-N-(2-((tetrahydro-2H-pyran-2-yl)oxy) ethyl) carbamimidate (1.75 g, 4.36 mmol) in methanol (12 mL) was added hydrazine hydrate 25% in H$_2$O (873 mg, 864.00 µl, 4.36 mmol). The reaction mixture was stirred at 35° C. for 1 hour and then evaporated in vacuo to give N3-(3,4-Difluorophenyl)-N3-(2-((tetrahydro-2H-pyran-2-yl)oxy)ethyl)-4H-1,2,4-triazole-3,5-diamine (1.79 g, 91%) which was used directly for the next step without further purification. (1.79 g, 91%). MS (ES+) m/z: 340.2 [M+H]$^+$.

Step 4: The crude of N3-(3,4-difluorophenyl)-N3-(2-((tetrahydro-2H-pyran-2-yl)oxy)ethyl)-4H-1,2,4-triazole-3,5-diamine (1.79 g, 5.27 mmol) was dissolved in a mixture of aqueous HCl 2M (9 mL) an methanol (43 mL). The reaction mixture was stirred at RT for 1 hour and concentrated in vacuo. The residue was diluted with EtOAc and washed with an aqueous NaHCO$_3$ solution. The organic layer was dried Na$_2$SO$_4$ and the product purified by combiflash chromatography (CH$_2$Cl$_2$:MeOH 100:0 to 90:10) to afford 2-((5-Amino-4H-1,2,4-triazol-3-yl)(3,4-difluorophenyl)amino) ethanol as a white solid (0.39 g, 29%). MS (ES+) m/z: 256.2 [M+H]$^+$.

Step 5: To a THF (4 mL) solution of 2-((5-Amino-4H-1,2,4-triazol-3-yl)(3,4-difluorophenyl) amino)ethanol (50.00 mg, 196 µmol) and triphenylphosphine (154 mg, 588 µmol) was added DEAD (70 mg, 64 µl, 392 µmol) the reaction was stirred at RT for 24 hours. The reaction was stirred for further 7 hours at 50° C. and then one extra amount of triphenylphosphine (154 mg, 588 µmol), DEAD (70 mg, 64 µl, 392 µmol) and THF (4 mL) were added. The reaction mixture was left to stir at RT overnight. The mixture was diluted with EtOAc and washed three times with water and brine; the organic phase was dried over sodium sulfate, filtered and evaporated in vacuo. The crude was purified using combiflash chromatography (CH$_2$Cl$_2$:MeOH 100:0 to 90:10) to afford 4-(3,4-difluorophenyl)-5,6-dihydro-4H-imidazo[1,2-b][1,2,4]triazol-2-amine as a white solid (7.2 mg, 15%). MS (ES+) m/z: 238.1 [M+H]$^+$.

Step 6: tert-Butyl nitrile (232 mg, 268 µl, 2.0 mmol) and cupric bromide (452 mg, 96 µl, 2.0 mmol) were combined in CH$_3$CN (40 mL) and stirred at 60° C. before a solution of 4-(3,4-difluorophenyl)-5,6-dihydro-4H-imidazo[1,2-b][1,2,4]triazol-2-amine (140 mg, 590 µmol) in CH$_3$CN (40 mL) was added drop wise. The reaction mixture was stirred at 75° C. for 2 hours, concentrated in vacuo, diluted with 1M HCl and extracted three times with EtOAc. The combined organic layer was dried over sodium sulfate, filtered and evaporated in vacuo. The crude was purified by combiflash chromatography (Hept:EtOAc 100:0 to 50:50) to afford 2-bromo-4-(3,4-difluorophenyl)-5,6-dihydro-4H-imidazo[1,2-b][1,2,4]triazole (0.12 g, 69%) as an off-white solid. MS (ES+) m/z: 301.0 and 303.0 [M+H]$^+$. (Br isotopes).

Intermediate 9-2:

2-bromo-4-[4-(trifluoromethyl)phenyl]-5,6-dihydroimidazo[1,2-b][1,2,4]triazole

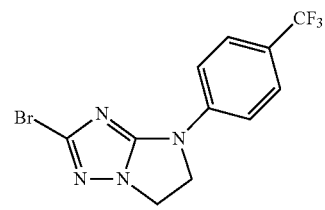

9-2

In analogy to the preparation of the intermediate 9-1, starting from 4-(trifluoromethyl)aniline was prepared 0.12 g of the intermediate 2-bromo-4-[4-(trifluoromethyl)phenyl]-5,6-dihydro imidazo[1,2-b][1,2,4]triazole (9-2) as a white solid. MS (ES+) m/z: 333.0 and 335.0 [M+H]$^+$. (Br isotopes)

Intermediate 9-3:

2-bromo-4-(2,3,4-trifluorophenyl)-5,6-dihydroimidazo[1,2-b][1,2,4]triazole

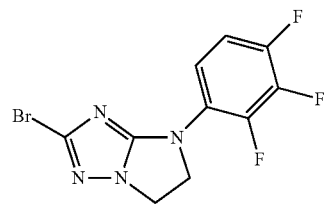

9-3

In analogy to the preparation of the intermediate 9-1, starting from 2,3,4-trifluoroaniline was prepared 0.12 g of the intermediate 2-bromo-4-(2,3,4-trifluorophenyl)-5,6-dihydroimidazo[1,2-b][1,2,4]triazole (9-3) as a white solid. MS (ES+) m/z: 319.0 and 321.0 [M+H]$^+$. (Br isotopes)

Intermediates of Type 15

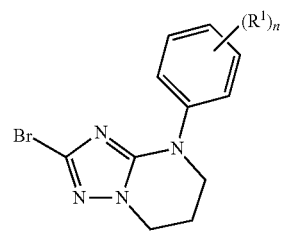

Intermediate 15-1:

2-bromo-4-(3,4-difluorophenyl)-6,7-dihydro-5H-[1,2,4]triazolo[1,5-a]pyrimidine

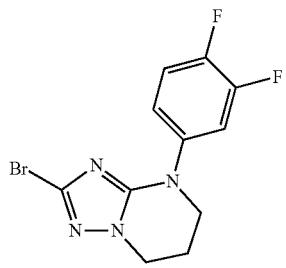

15-1

Step 1: 3,4-Difluoroaniline (3.00 g, 23.20 mmol) and diphenyl cyanocarbonimidate (5.53 g, 23.20 mmol) were dissolved in 2-propanol (64.00 mL). The reaction mixture was stirred at RT overnight. The crude was evaporated in vacuo and purified by column chromatography (Hept:EtOAc 100:0 to 50:50) to afford (Z)-phenyl N'-cyano-N-(3,4-difluorophenyl) carbamimidate as a white solid (5.00 g, 79%). MS (ES+) m/z: 274.1 [M+H]$^+$.

Step 2: A solution of (Z)-phenyl N'-cyano-N-(3,4-difluorophenyl)carbamimidate (17.69 g, 64.70 mmol), 2-(3-bromopropoxy)tetrahydro-2H-pyran (22.80 g, 17.10 mL, 97.10 mmol) and K$_2$CO$_3$ (17.90 g, 129.00 mmol) in DMF (200 mL) was heated overnight at 85° C. The reaction mixture was concentrated in vacuo and the residue was purified by column chromatography (Hept:EtOAc 90:10 to 50:50) to give 3-cyano-1-(3,4-difluorophenyl)-2-phenyl-1-(3-tetrahydropyran-2-yloxypropyl)isourea as a white solid (26.90 g, 49%). MS (ES+) m/z: 416.2 [M+H]$^+$.

Step 3: To a solution of of (Z)-phenyl N'-cyano-N-(3,4-difluorophenyl)-N-(3-((tetrahydro-2H-pyran-2-yl)oxy)propyl)carbamimidate (10.20 g, 24.60 mmol) in MeOH (70 mL) was added hydrazine hydrate 25% in water (4.92 g, 4.87 mL, 24.60 mmol). The reaction mixture was stirred at RT overnight, evaporated and purified by column chromatography (CH$_2$Cl$_2$:MeOH 99:1 to 92.5:7.5) to afford N3-(3,4-difluorophenyl)-N3-(3-tetrahydropyran-2-yloxypropyl)-4H-1,2,4-triazole-3,5-diamine as a colourless foam (8.68 g, 78%). MS (ES+) m/z: 354.2 [M+H]$^+$.

Step 4: To a solution of N3-(3,4-difluorophenyl)-N3-(3-((tetrahydro-2H-pyran-2-yl)oxy)propyl)-4H-1,2,4-triazole-3,5-diamine (6.75 g, 19.10 mmol) in MeOH (150 mL) followed by addition of aqueous HCl 2M (30 mL). The reaction mixture was stirred at RT for 90 minutes and concentrated in vacuo. The residue was diluted with EtOAc and washed with an aqueous NaHCO$_3$ solution. The organic layer was dried on Na$_2$SO$_4$ and the product purified by combiflash chromatography to afford 3-(N-(5-Amino-4H-1,2,4-triazol-3-yl)-3,4-difluoro-anilino)propan-1-ol as a white solid (5.14 g, 95%). MS (ES+) m/z: 270.1 [M+H]$^+$.

Step 5: To a solution of 3-((5-amino-4H-1,2,4-triazol-3-yl)(3,4-difluorophenyl)amino) propan-1-ol (4.55 g, 16.90 mmol) in DMF (90 mL) at −15/−20° C., was added triphenylphosphine (6.65 g, 25.30 mmol). The mixture was stirred at −15/−20° C. for 15 minutes, then at −30° C., DEAD (4.55 g, 4.10 ml, 25.30 mmol) was added drop wise over of 20 minutes. The mixture was stirred at −30° C. for 90 minutes. Water was added to the reaction mixture and then concentrated under vacuo, and the product extracted with EtOAc. The combined organic layers were washed once with brine, dried over sodium sulfate, filtered and evaporated in vacuo. The crude was purified using silica chromatography (CH$_2$Cl$_2$:MeOH 99:1 to 96:4) to afford 4-(3,4-difluorophenyl)-6,7-dihydro-5H-[1,2,4]triazolo[1,5-a]pyrimidin-2-amine as a white solid (3.41 g, 80%). MS (ES+) m/z: 252.1 [M+H]$^+$.

Step 6: To a black solution of tert-butyl nitrite (1.01 g, 1.17 mL, 8.86 mmol) and cupric bromide (1.98 g, 420 µl, 8.86 mmol) in CH$_3$CN (150 mL) at 60° C., 4-(3,4-difluorophenyl)-4,5,6,7-tetrahydro-[1,2,4]triazolo[1,5-a]pyrimidin-2-amine (1.63 g, 5.90 mmol,) in 50 mL CH$_3$CN was added drop wise. After addition, the reaction mixture was heated to 75° C. and stirred for 30 minutes. The reaction mixture was concentrated in vacuo, diluted with 2 mL of 1M HCl and extracted 3 times with EtOAc. The organic layers were dried over sodium sulfate and concentrated. The crude was purified by chromatography (CH$_2$Cl$_2$:MeOH 99.5:0.5) to afford 2-bromo-4-(3,4-difluorophenyl)-6,7-dihydro-5H-[1,2,4]triazolo[1,5-a]pyrimidine as a light yellow solid (1.86 g, 82%). MS (ES+) m/z: 315.0 and 317.0 [M+H]$^+$. (Br isotopes).

Intermediate 15-2:

2-bromo-4-[4-(trifluoromethyl)phenyl]-6,7-dihydro-5H-[1,2,4]triazolo[1,5-a]pyrimidine

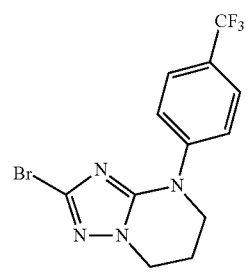

15-2

In analogy to the preparation of the intermediate 15-1, starting from 4-(trifluoromethyl)aniline was prepared 32 mg of the intermediate 2-bromo-4-[4-(trifluoromethyl)phenyl]-6,7-dihydro-5H-[1,2,4]triazolo[1,5-a]pyrimidine (15-2) as a white solid. MS (ES+) m/z: 347.0 and 349.0 [M+H]$^+$. (Br isotopes).

Intermediate 15-3:

2-bromo-4-(3,5-difluorophenyl)-6,7-dihydro-5H-[1,2,4]triazolo[1,5-a]pyrimidine

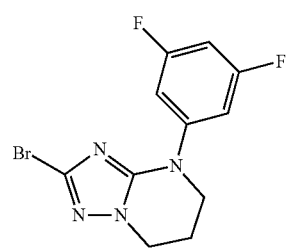

15-3

In analogy to the preparation of the intermediate 15-1, starting from 3,5-difluoroaniline was prepared 234 mg of the intermediate 2-bromo-4-(3,5-difluorophenyl)-6,7-dihydro-5H-[1,2,4]triazlo[1,5-a]pyrimidine (15-3) as a white solid. MS (ES+) m/z: 315.0 and 317.0 [M+H]+. (Br isotopes).

Intermediate 15-4:

2-bromo-4-(3-fluoro-4-methyl-phenyl)-6,7-dihydro-5H-[1,2,4]triazolo[1,5-a]pyrimidine

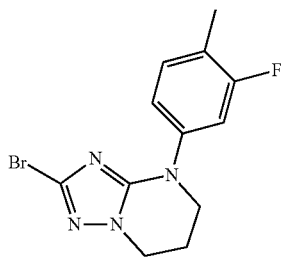

15-4

In analogy to the preparation of the intermediate 15-1, starting from 3-fluoro-4-methyl-aniline was prepared 662 mg of the intermediate 2-bromo-4-(3-fluoro-4-methyl-phenyl)-6,7-dihydro-5H-[1,2,4]triazolo[1,5-a]pyrimidine (15-4) as a light yellow oil. MS (ES+) m/z: 311.0 and 313.0 [M+H]+. (Br isotopes).

Intermediate 15-5:

2-bromo-4-(2,3,4-trifluorophenyl)-6,7-dihydro-5H-[1,2,4]triazolo[1,5-a]pyrimidine

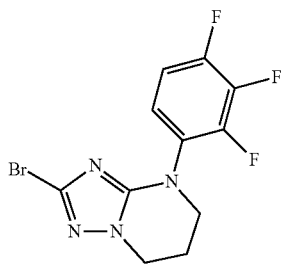

15-5

In analogy to the preparation of the intermediate 15-1, starting from 2,3,4-trifluoroaniline was prepared 134 mg of the intermediate 2-bromo-4-(2,3,4-trifluorophenyl)-6,7-dihydro-5H-[1,2,4]triazolo[1,5-a]pyrimidine (15-5) as a light brown solid. MS (ES+) m/z: 333.0 and 335.0 [M+H]+. (Br isotopes).

Intermediate 15-6:

2-bromo-4-(3-fluorophenyl)-6,7-dihydro-5H-[1,2,4]triazolo[1,5-a]pyrimidine

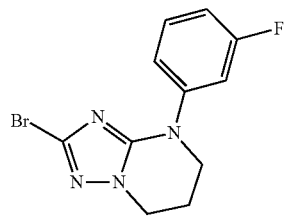

15-6

In analogy to the preparation of the intermediate 15-1, starting from 3-fluoroaniline was prepared 210 mg of the intermediate 2-bromo-4-(3-fluorophenyl)-6,7-dihydro-5H-[1,2,4]triazolo[1,5-a]pyrimidine (15-6) as a light yellow solid. MS (ES+) m/z: 297.0 and 299.0 [M+H]+. (Br isotopes).

Intermediate 15-7:

2-bromo-4-(4-fluorophenyl)-6,7-dihydro-5H-[1,2,4]triazolo[1,5-a]pyrimidine

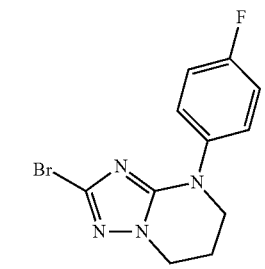

15-7

In analogy to the preparation of the intermediate 15-1, starting from 4-fluoroaniline was prepared 1.11 g of the intermediate 2-bromo-4-(4-fluorophenyl)-6,7-dihydro-5H-[1,2,4]triazolo[1,5-a]pyrimidine (15-7) as a light yellow solid. MS (ES+) m/z: 297.0 and 299.0 [M+H]+. (Br isotopes).

Intermediate 15-8:

2-bromo-4-(3-chlorophenyl)-6,7-dihydro-5H-[1,2,4]triazolo[1,5-a]pyrimidine

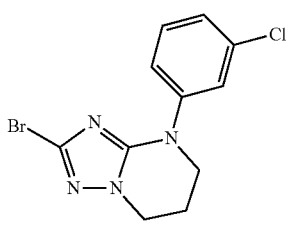

15-8

In analogy to the preparation of the intermediate 15-1, starting from 3-chloroaniline was prepared 1.06 g of the intermediate 2-bromo-4-(3-chlorophenyl)-6,7-dihydro-5H-

[1,2,4]triazolo[1,5-a]pyrimidine (15-8) as a white solid. MS (ES+) m/z: 313.0 and 315.0 [M+H]⁺. (Br isotopes).

Intermediate 15-9:

2-bromo-4-(2-fluorophenyl)-6,7-dihydro-5H-[1,2,4]triazolo[1,5-a]pyrimidine

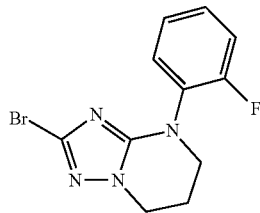

15-9

In analogy to the preparation of the intermediate 15-1, starting from 2-fluoroaniline was prepared 1.05 g of the intermediate 2-bromo-4-(2-fluorophenyl)-6,7-dihydro-5H-[1,2,4]triazolo[1,5-a]pyrimidine (15-9) as a white solid. MS (ES+) m/z: 297.1 and 299.1 [M+H]⁺. (Br isotopes).

Intermediate 15-10:

2-bromo-4-[2-(trifluoromethyl)phenyl]-6,7-dihydro-5H-[1,2,4]triazolo[1,5-a]pyrimidine

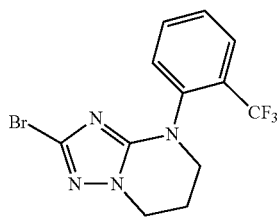

15-10

In analogy to the preparation of the intermediate 15-1, starting from 2-(trifluoromethyl)aniline was prepared 0.90 g of the intermediate 2-bromo-4-[2-(trifluoromethyl)phenyl]-6,7-dihydro-5H-[1,2,4]triazolo[1,5-a]pyrimidine (15-10) as a white solid. MS (ES+) m/z: 347.1 and 349.1 [M+H]⁺. (Br isotopes).

Intermediate 15-11:

2-bromo-4-(4-chlorophenyl)-6,7-dihydro-5H-[1,2,4]triazolo[1,5-a]pyrimidine

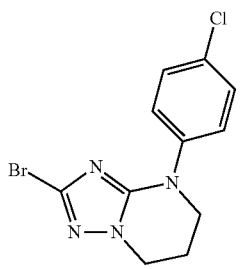

15-11

In analogy to the preparation of the intermediate 15-1, starting from 4-chloroaniline was prepared 1.2 g of the intermediate 2-bromo-4-(4-chlorophenyl)-6,7-dihydro-5H-[1,2,4]triazolo[1,5-a]pyrimidine (15-11) as a white solid. MS (ES+) m/z: 313.1 and 315.1 [M+H]⁺. (Br isotopes).

Intermediate 15-12:

2-bromo-4-phenyl-6,7-dihydro-5H-[1,2,4]triazolo[1,5-a]pyrimidine

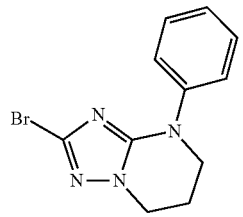

15-12

In analogy to the preparation of the intermediate 15-1, starting from aniline was prepared 240 mg of the intermediate 2-bromo-4-phenyl-6,7-dihydro-5H-[1,2,4]triazolo[1,5-a]pyrimidine (15-12) as a white solid. MS (ES+) m/z: 279.0 and 281.0 [M+H]⁺. (Br isotopes).

Intermediate 15-13:

2-bromo-4-(4-methoxyphenyl)-6,7-dihydro-5H-[1,2,4]triazolo[1,5-a]pyrimidine

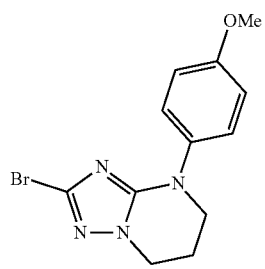

15-13

In analogy to the preparation of the intermediate 15-1, starting from 4-methoxyaniline was prepared 1.05 g of the intermediate 2-bromo-4-(4-methoxyphenyl)-6,7-dihydro-5H-[1,2,4]triazolo[1,5-a]pyrimidine (15-13) as a white solid. MS (ES+) m/z: 309.1 and 311.1 [M+H]⁺. (Br isotopes).

Intermediate 15-14:

2-bromo-4-[4-(trifluoromethoxy)phenyl]-6,7-dihydro-5H-[1,2,4]triazolo[1,5-a]pyrimidine

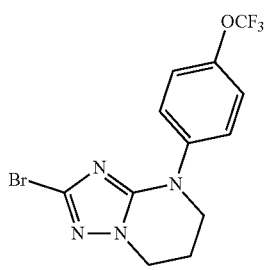

15-14

In analogy to the preparation of the intermediate 15-1, starting from 4-(trifluoromethoxy)aniline was prepared 1.10 g of the intermediate 2-bromo-4-[4-(trifluoromethoxy)phenyl]-6,7-dihydro-5H-[1,2,4]triazolo[1,5-a]pyrimidine (15-14) as a white solid. MS (ES+) m/z: 363.1 and 365.1 [M+H]+. (Br isotopes).

Intermediate 15-15:

2-bromo-4-(2-chlorophenyl)-6,7-dihydro-5H-[1,2,4]triazolo[1,5-a]pyrimidine

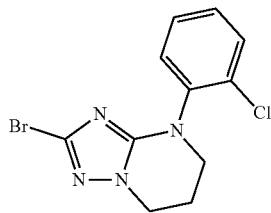

15-15

In analogy to the preparation of the intermediate 15-1, starting from 2-chloroaniline was prepared 1.06 g of the intermediate 2-bromo-4-(2-chlorophenyl)-6,7-dihydro-5H-[1,2,4]triazolo[1,5-a]pyrimidine (15-15) as a white solid. MS (ES+) m/z: 313.0 and 315.0 [M+H]+. (Br isotopes).

Intermediates of Type 20

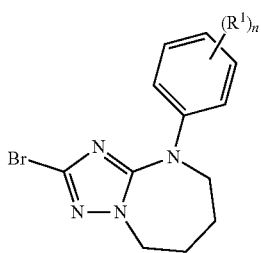

Intermediate 20-1:

2-bromo-4-(3,4-difluorophenyl)-5,6,7,8-tetrahydro-[1,2,4]triazolo[1,5-a][1,3]diazepine

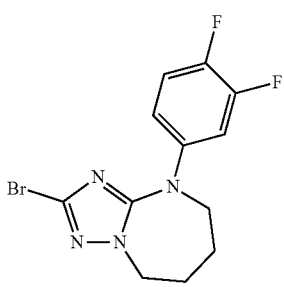

20-1

Step 1: 3,4-Difluoroaniline (3.00 g, 23.20 mmol) and diphenyl cyanocarbonimidate (5.53 g, 23.20 mmol) were dissolved in 2-propanol (64.00 mL). The reaction mixture was stirred at RT overnight. The crude was evaporated in vacuo and purified by column chromatography (Hept:EtOAc 100:0 to 50:50) to afford (Z)-phenyl N'-cyano-N-(3,4-difluorophenyl) carbamimidate as a white solid (5.00 g, 79%). MS (ES+) m/z: 274.1 [M+H]+.

Step 2: A solution of (Z)-phenyl N'-cyano-N-(3,4-difluorophenyl)carbamimidate (10.0 g, 36.6 mmol), 2-(3-bromobutoxy)tetrahydro-2H-pyran (13.30 g, 54.90 mmol) and K2CO3 (10.10 g, 73.20 mmol) in DMF (350 mL) was heated overnight at 85° C. The reaction mixture was concentrated in vacuo and the residue was purified by column chromatography (Hept:EtOAc 90:10 to 50:50) to give 3-cyano-1-(3,4-difluorophenyl)-2-phenyl-1-(4-tetrahydropyran-2-yloxybutyl)isourea as a colorless oil (5.31 g, 34%). MS (ES+) m/z: 430.2 [M+H]+.

Step 3: To a solution of 3-cyano-1-(3,4-difluorophenyl)-2-phenyl-1-(4-tetrahydropyran-2-yloxybutyl)isourea (5.29 g, 12.30 mmol) in MeOH (40 mL) was added hydrazine hydrate 25% in water (2.47 g, 2.44 mL, 12.30 mmol). The reaction mixture was stirred at RT for 7 hours, evaporated and purified by column chromatography (CH2Cl2:MeOH 99:1 to 92.5:7.5) to afford N3-(3,4-difluorophenyl)-N3-(3-tetrahydropyran-2-yloxybutyl)-4H-1,2,4-triazole-3,5-diamine as a colourless oil (3.54 g, 78%). MS (ES+) m/z: 368.2 [M+H]+.

Step 4: To a solution of N3-(3,4-difluorophenyl)-N3-(3-tetrahydropyran-2-yloxybutyl)-4H-1,2,4-triazole-3,5-diamine (3.50 g, 9.53 mmol) in MeOH (85 mL) was added an aqueous HCl 2M solution (17 mL). The reaction mixture was stirred at RT for 90 minutes and concentrated in vacuo. The residue was diluted with EtOAc and washed with an aqueous NaHCO3 solution. The organic layer was dried on Na2SO4 and the product purified by combiflash chromatography to afford 4-(N-(5-amino-4H-1,2,4-triazol-3-yl)-3,4-difluoro-anilino)butan-1-ol as a white solid (2.51 g, 93%). MS (ES+) m/z: 284.1 [M+H]+.

Step 5: At 0° C., cyanomethylenetrimethylphosphorane 0.5 M in THF (8.47 mL, 4.24 mmol) was added drop wise within 15 minutes to a solution of 4-((5-amino-4H-1,2,4-triazol-3-yl)(3,4-difluorophenyl)amino)butan-1-ol (1.00 g, 3.53 mmol) in THF (120 mL) at 0° C. and stirred at RT overnight. The mixture was concentrated under vacuo, and the crude diluted with EtOAc and washed with water. The organic layer was dried over sodium sulfate, filtered and evaporated in vacuo. The crude was purified using silica chromatography (CH2Cl2:MeOH 99:1 to 96:4) to afford 4-(3,4-difluorophenyl)-5,6,7,8-tetrahydro-[1,2,4]triazolo[1,5-a][1,3]diazepin-2-amine as a white solid (0.2 g, 21%). MS (ES+) m/z: 266.1 [M+H]+.

Step 6: To a black solution of tert-butyl nitrite (115 mg, 0.13 mL, 1.01 mmol) and cupric bromide (225 mg, 47.7 µl, 1.01 mmol) in CH3CN (15 mL) at 60° C., 4-(3,4-difluorophenyl)-5,6,7,8-tetrahydro-[1,2,4]triazolo[1,5-a][1,3]diazepin-2-amine (178 mg, 0.671 mmol,) in 25 mL CH3CN was added drop wise. After addition, the reaction mixture was heated to 75° C. and stirred for 30 minutes. The reaction mixture was concentrated in vacuo, diluted with 2 mL of 1M HCl and extracted 3 times with EtOAc. The organic layers were dried over sodium sulfate and concentrated. The crude was purified by chromatography (CH2Cl2:MeOH 99.5:0.5) to afford 2-bromo-4-(3,4-difluorophenyl)-5,6,7,8-tetrahydro-[1,2,4]triazolo[1,5-a][1,3]diazepine as a light yellow oil (0.13 g, 58%). MS (ES+) m/z: 329.0 and 331.0 [M+H]+. (Br isotopes).

Intermediate 20-2:

2-bromo-4-[4-(trifluoromethyl)phenyl]-5,6,7,8-tetrahydro-[1,2,4]triazolo[1,5-a][1,3]diazepine

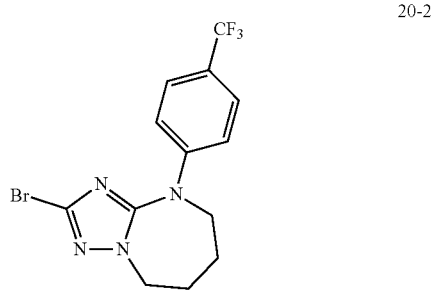 [SMILES: FC(F)(F)c1ccc(N2CCCCn3nc(Br)nc32)cc1]

In analogy to the preparation of the intermediate 20-1, starting from 4-(trifluoromethyl)aniline was prepared 72 mg of the intermediate 2-bromo-4-[4-(trifluoromethyl)phenyl]-5,6,7,8-tetrahydro-[1,2,4]triazolo[1,5-a][1,3]diazepine (20-2) as a white solid. MS (ES+) m/z: 361.0 and 363.0 [M+H]$^+$. (Br isotopes).

Intermediates of Type 10

Intermediate 10-1:

(1R,5S,8S)-3-(6-methylpyrimidin-4-yl)-3-azabicyclo[3.2.1]octan-8-amine

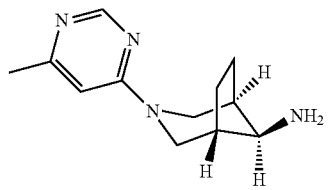 [SMILES: Cc1cc(N2C[C@H]3CC[C@@H](C2)[C@@H]3N)ncn1]

Step 1: In a sealed tube tert-butyl N-[(1R,5S,8S)-3-azabicyclo[3.2.1]octan-8-yl]carbamate (500 mg, 2.21 mmol) was dissolved in EtOH (10 mL) and 4-chloro-6-methylpyrimidine (869 mg, 6.63 mmol) was added followed by triethylamine (894 mg, 1.23 mL, 8.84 mmol). The reaction mixture was stirred at 130° C. overnight. The crude reaction mixture was concentrated in vacuum. The residue was diluted with 20 mL of CH$_2$Cl$_2$ and 20 mL of water. The organic phase was extracted with CH$_2$Cl$_2$ (3×20 mL), dried over MgSO$_4$ and concentrated in vacuum. The crude material was purified by flash chromatography (0% to 100% EtOAc in heptane) to afford tert-butyl N-[(1R,5S,8S)-3-(6-methylpyrimidin-4-yl)-3-azabicyclo[3.2.1]octan-8-yl]carbamate as a yellow solid (496 mg, 71% yield). MS (ES+) m/z: 319.2 [(M+H)$^+$].

Step 2: To a light yellow solution of tert-butyl N-[(1R,5S,8S)-3-(6-methylpyrimidin-4-yl)-3-azabicyclo[3.2.1]octan-8-yl]carbamate (260 mg, 817 μmol) in CH$_2$Cl$_2$ (8 mL) was added TFA (931 mg, 629 μl, 8.17 mmol). The reaction mixture was stirred at room temperature over night and concentrated in vacuum. The crude material was purified by Ion-exchange column (Si-SCX-2, 10 g, washed with MeOH and liberated with MeOH (NH$_3$ 2M)) to afford (1R,5S,8S)-3-(6-methylpyrimidin-4-yl)-3-azabicyclo[3.2.1]octan-8-amine 10-1 (195 mg, 804 μmol, 98.5% yield) that was used in the next step without further purification. MS (ES+) m/z: 219.2 [(M+H)$^+$]

Intermediate 10-2:

(1R,5S,8S)-3-(5-fluoro-6-methyl-pyrimidin-4-yl)-3-azabicyclo[3.2.1]octan-8-amine

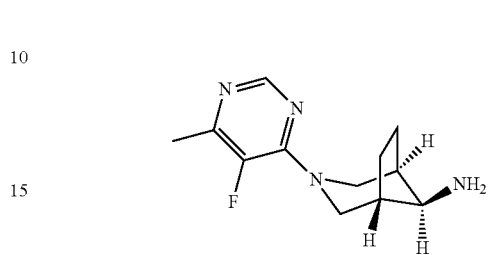

Step 1: In analogy to the preparation of the intermediate 10-1 (step 1) from tert-butyl N-[(1R,5S,8S)-3-azabicyclo[3.2.1]octan-8-yl]carbamate (200 mg, 884 μmol) and 4-chloro-5-fluoro-6-methylpyrimidine (194 mg, 1.33 mmol) in a sealed tube at 100° C. and EtOH as solvent in the presence of triethylamine (358 mg, 493 μl, 3.53 mmol), tert-butyl N-[(1R,5S,8S5)-3-(5-fluoro-6-methyl-pyrimidin-4-yl)-3-azabicyclo[3.2.1]octan-8-yl]carbamate was obtained as a white solid (255 mg, 758 μmol, 86% yield). MS (ES+) m/z: 337.3 [(M+H)$^+$].

Step 2: In analogy to the preparation of intermediate 10-1 (step 2) from tert-butyl N-[(1R,5S,8S)-3-(5-fluoro-6-methyl-pyrimidin-4-yl)-3-azabicyclo[3.2.1]octan-8-yl]carbamate (253 mg, 752 μmol) in CH$_2$Cl$_2$ in the presence of aqueous HCl 37% (445 mg, 371 μl, 4.51 mmol), (1R,5S,8S)-3-(5-fluoro-6-methyl-pyrimidin-4-yl)-3-azabicyclo[3.2.1]octan-8-amine (170 mg, 719 μmol, 96% yield) was obtained as a white solid and used directly in the next step without further purification. MS (ES+) m/z: 237.1 [(M+H)$^+$].

Intermediate 10-3:

(1R,5S,8S)-3-(6-chloropyrimidin-4-yl)-3-azabicyclo[3.2.1]octan-8-amine

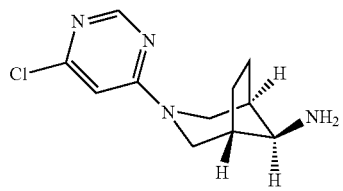 [SMILES: N[C@@H]1[C@@H]2CC[C@H]1CN(c1cc(Cl)ncn1)C2]

Step 1: In analogy to the preparation of the intermediate 10-1 (step 1) from tert-butyl N-[(1R,5S,8S)-3-azabicyclo[3.2.1]octan-8-yl]carbamate (250 mg, 1.1 mmol) and 4-chloro-6-fluoro-pyrimidine (220 mg, 1.66 mmol) in a sealed tube at 100° C. using EtOH as solvent in the presence of triethylamine (447 mg, 616 μl, 4.42 mmol), tert-butyl N-[(1R,5S,8S)-3-(6-chloropyrimidin-4-yl)-3-azabicyclo[3.2.1]octan-8-yl]carbamate (329 mg, 88% yield) was obtained as a white solid. MS (ES+) m/z: 339.2 [(M+H)$^+$].

Step 2: In analogy to the preparation of intermediate 10-1 (step 2) from tert-butyl N-[(1R,5S,8S)-3-(6-chloropyrimidin-4-yl)-3-azabicyclo[3.2.1]octan-8-yl]carbamate (325 mg, 959 μmol) in CH$_2$Cl$_2$ in the presence of HCl 37% (567 mg, 473 µl, 5.76 mmol), (1R,5S,8S)-3-(6-chloropyrimidin-4-yl)-3-azabicyclo[3.2.1]octan-8-amine (230 mg, 100% yield) was obtained as a white solid and used directly in the next step without further purification. MS (ES+) m/z: 239.2 [(M+H)⁺].

Intermediate 10-4:

(1R,5S,8S)-3-(6-methoxypyrimidin-4-yl)-3-azabicyclo[3.2.1]octan-8-amine

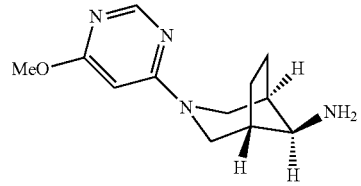 [SMILES: COc1cc(N2C[C@H]3CC[C@@H](C2)[C@@H]3N)ncn1]

Step 1: In analogy to the preparation of the intermediate 10-1 (step 1) from tert-butyl N-[(1R,5S,8S)-3-azabicyclo[3.2.1]octan-8-yl]carbamate (250 mg, 1.1 mmol) and 4-iodo-6-methoxypyrimidine (391 mg, 1.66 mmol) in a sealed tube at 100° C. using DMF as solvent in the presence of K$_2$CO$_3$ (458 mg, 3.31 mmol), tert-butyl N-[(1R,5S,8S)-3-(6-methoxypyrimidin-4-yl)-3-azabicyclo[3.2.1]octan-8-yl]carbamate (315 mg, 85% yield) was obtained as a white solid. MS (ES+) m/z: 335.2 [(M+H)⁺].

Step 2: In analogy to the preparation of intermediate 10-1 (step 2) from tert-butyl N-[(1R,5S,8S)-3-(6-methoxypyrimidin-4-yl)-3-azabicyclo[3.2.1]octan-8-yl]carbamate (330 mg, 987 µmol) in CH$_2$Cl$_2$ in the presence of TFA (1.13 g, 760 µl, 9.87 mmol), (1R,5S,8S)-3-(6-methoxypyrimidin-4-yl)-3-azabicyclo[3.2.1]octan-8-amine (222 mg, 96% yield) was obtained as a white solid and used directly in the next step without further purification. MS (ES+) m/z: 235.2 [(M+H)⁺].

Intermediate 10-5:

(1R,5S,8S)-3-[2-(trifluoromethyl)-4-pyridyl]-3-azabicyclo[3.2.1]octan-8-amine

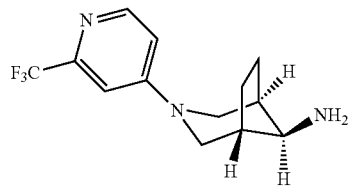 [SMILES: N[C@@H]1[C@@H]2CC[C@H]1CN(c1ccnc(C(F)(F)F)c1)C2]

Step 1: In analogy to the preparation of the intermediate 10-1 (step 1) from tert-butyl N-[(1R,5S,8S)-3-azabicyclo[3.2.1]octan-8-yl]carbamate (1.57 g, 6.87 mmol) and 4-iodo-2-(trifluoromethyl)pyridine (1.5 g, 5.33 mmol) in a sealed tube at 150° C. using NMP as solvent in the presence of DIPEA (964 mg, 1.3 ml, 7.46 mmol), tert-butyl N-[(1R,5S,8S)-3-[2-(trifluoromethyl)-4-pyridyl]-3-azabicyclo[3.2.1]octan-8-yl]carbamate (1.37 g, 70% yield) was obtained as a white solid. MS (ES+) m/z: 372.2 [(M+H)⁺].

Step 2: In analogy to the preparation of intermediate 10-1 (step 2) from tert-butyl N-[(1R,5S,8S)-3-[2-(trifluoromethyl)-4-pyridyl]-3-azabicyclo[3.2.1]octan-8-yl]carbamate (1.05 g, 2.82 mmol) in CH$_2$Cl$_2$ in the presence of HCl 37% (1.68 g, 1.4 mL, 17 mmol), (1R,5S,8S)-3-[2-(trifluoromethyl)-4-pyridyl]-3-azabicyclo[3.2.1]octan-8-amine (735 mg, 96% yield) was obtained as a white solid and used directly in the next step without further purification. MS (ES+) m/z: 272.2 [(M+H)⁺].

Intermediate 10-6:

(1R,5S,8S)-3-(2-chloro-4-pyridyl)-3-azabicyclo[3.2.1]octan-8-amine

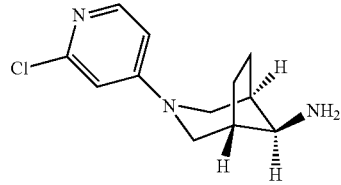 [SMILES: N[C@@H]1[C@@H]2CC[C@H]1CN(c1ccnc(Cl)c1)C2]

Step 1: In analogy to the preparation of the intermediate 10-1 (step 1) from tert-butyl N-[(1R,5S,8S)-3-azabicyclo[3.2.1]octan-8-yl]carbamate (120 mg, 0.53 mmol) and 2-chloro-4-fluoro-pyridine (76 mg, 0.58 mmol) in a sealed tube at 150° C. using NMP as solvent in the presence of DIPEA (137 mg, 0.185 ml, 1.06 mmol), tert-butyl N-[(1R,5S,8S)-3-(2-chloro-4-pyridyl)-3-azabicyclo[3.2.1]octan-8-yl]carbamate (150 mg, 82% yield) was obtained as a white solid. MS (ES+) m/z: 338.2 [(M+H)⁺].

Step 2: In analogy to the preparation of intermediate 10-1 (step 2) from tert-butyl N-[(1R,5S,8S)-3-[2-(trifluoromethyl)-4-pyridyl]-3-azabicyclo[3.2.1]octan-8-yl]carbamate (147 mg, 435 µmol) in CH$_2$Cl$_2$ in the presence of HCl 37% (257 mg, 214 µl, 2.61 mmol), (1R,5S,8S)-3-(2-chloro-4-pyridyl)-3-azabicyclo[3.2.1]octan-8-amine (90 mg, 87% yield) was obtained as a white solid and used directly in the next step without further purification. MS (ES+) m/z: 238.1 [(M+H)⁺].

Intermediate 10-7:

(1R,5S,8S)-3-(2-methoxy-4-pyridyl)-3-azabicyclo[3.2.1]octan-8-amine

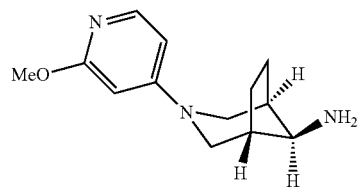 [SMILES: COc1cc(N2C[C@H]3CC[C@@H](C2)[C@@H]3N)ccn1]

Step 1: In analogy to the preparation of the intermediate 10-1 (step 1) from tert-butyl N-[(1R,5S,8S)-3-azabicyclo[3.2.1]octan-8-yl]carbamate (2.00 g, 8.84 mmol) and 4-fluoro-2-methoxypyridine (1.12 g, 8.84 mmol) in a sealed tube at 140° C. using NMP as solvent in the presence of DIPEA (2.28 g, 3.09 mL, 17.70 mmol), tert-butyl N-[(1R,5S,8S)-3-(2-methoxy-4-pyridyl)-3-azabicyclo[3.2.1]octan-8-yl]carbamate (1.42 g, 48%) was obtained as a white solid. MS (ES+) m/z: 334.3 [(M+H)⁺].

Step 2: In analogy to the preparation of intermediate 10-1 (step 2) from tert-butyl N-[(1R,5S,8S)-3-(2-methoxy-4-pyridyl)-3-azabicyclo[3.2.1]octan-8-yl]carbamate (1.42 g, 4.26 mmol) in CH$_2$Cl$_2$ in the presence of TFA (7.38 g, 5.0 mL, 15.2 mmol), (1R,5S,8S)-3-(2-methoxy-4-pyridyl)-3-azabicyclo[3.2.1]octan-8-amine (0.89 g, 89%) was obtained as a white solid and used directly in the next step without further purification. MS (ES+) m/z: 234.2 [(M+H)+].

Intermediate 10-8:

(1R,5S,8S)-3-(6-chloropyridazin-4-yl)-3-azabicyclo[3.2.1]octan-8-amine

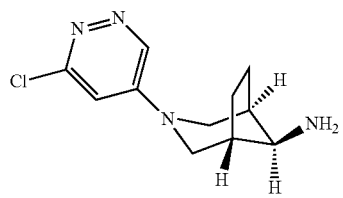 [SMILES: N[C@@H]1[C@@H]2CC[C@H]1CN(c1cnnc(Cl)c1)C2]

Step 1: In analogy to the preparation of the intermediate 10-1 (step 1) from tert-butyl N-[(1R,5S,8S)-3-azabicyclo[3.2.1]octan-8-yl]carbamate (2.00 g, 8.84 mmol) and 3,5-dichloropyridazine (2.0 g, 13.4 mmol) in a sealed tube at 90° C. using EtOH as solvent in the presence of Et$_3$N (3.63 g, 5.0 mL, 35.9 mmol), tert-butyl N-[(1R,5S,8S)-3-(6-chloropyridazin-4-yl)-3-azabicyclo[3.2.1]octan-8-yl]carbamate (1.71 g, 54%) was obtained as a white solid. MS (ES+) m/z: 339.2 [(M+H)+].

Step 2: In analogy to the preparation of intermediate 10-1 (step 2) from tert-butyl N-[(1R,5S,8S)-3-(6-chloropyridazin-4-yl)-3-azabicyclo[3.2.1]octan-8-yl]carbamate (0.93 g, 2.72 mmol) in CH$_2$Cl$_2$ in the presence of HCl 37% (1.61 g, 1.34 mL, 16.3 mmol), (1R,5S,8S)-3-(6-chloropyridazin-4-yl)-3-azabicyclo[3.2.1]octan-8-amine (0.65 g, 100%) was obtained as a white solid and used directly in the next step without further purification. MS (ES+) m/z: 239.1 [(M+H)+].

Intermediate 10-9:

(1R,5S,8S)-3-(6-methoxypyridazin-4-yl)-3-azabicyclo[3.2.1]octan-8-amine

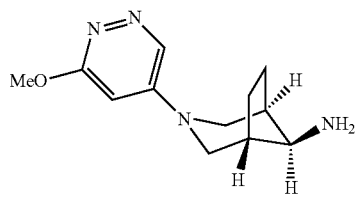 [SMILES: COc1cc(N2C[C@H]3CC[C@@H](C2)[C@@H]3N)cnn1]

Step 1: To a solution of tert-butyl N-[(1R,5S,8S)-3-(6-chloropyridazin-4-yl)-3-azabicyclo[3.2.1]octan-8-yl]carbamate (963 mg, 2.70 mmol) in MeOH (22 mL) in a sealed tube was added a methanol solution of NaOMe (25%, 1.9 mL, 8.3 mmol). The reaction mixture was heated at 85° C. over night. The reaction mixture was adsorbed on Isolute HM-N and a column chromatography gave tert-butyl N-[(1R,5S,8S)-3-(6-methoxypyridazin-4-yl)-3-azabicyclo[3.2.1]octan-8-yl]carbamate (362 mg, 38%) as a white solid. MS (ES+) m/z: 335.2 [(M+H)+].

Step 2: In analogy to the preparation of intermediate 10-1 (step 2) from tert-butyl N-[(1R,5S,8S)-3-(6-methoxypyridazin-4-yl)-3-azabicyclo[3.2.1]octan-8-yl]carbamate (0.93 g, 2.72 mmol) in CH$_2$Cl$_2$ in the presence of TFA (1.12 g, 0.76 mL, 9.86 mmol), (1R,5S,8S)-3-(6-methoxypyridazin-4-yl)-3-azabicyclo[3.2.1]octan-8-amine (225 mg, 96%) was obtained as a white solid and used directly in the next step without further purification. MS (ES+) m/z: 235.2 [(M+H)+].

Intermediate 10-10:

(1R,5S,8S)-3-(3-methyl-1,2,4-oxadiazol-5-yl)-3-azabicyclo[3.2.1]octan-8-amine

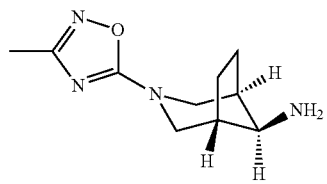

Step 1: To a light yellow solution of tert-butyl N-[(1R,5S,8S)-3-(6-chloropyridazin-4-yl)-3-azabicyclo[3.2.1]octan-8-yl]carbamate (250 mg, 1.1 mmol), in EtOH (4 mL) was added sodium bicarbonate (102 mg, 1.22 mmol) followed by cyanogen bromide (129 mg, 1.22 mmol). The reaction was stirred over night at room temperature and the suspension was filtered off and washed with some EtOH. The crude reaction mixture was concentrated in vacuum and the residue was purified by flash chromatography (silica gel, 12 g, 0% to 100% EtOAc in heptane) to afford tert-butyl N-[(1R,5S,8S)-3-cyano-3-azabicyclo[3.2.1]octan-8-yl]carbamate as a light yellow solid (216 mg, 78%). MS (ES+) m/z: 252.2 [(M+H)+].

Step 2: Tert-butyl N-[(1R,5S,8S)-3-cyano-3-azabicyclo[3.2.1]octan-8-yl]carbamate (200 mg, 796 μmol) was dissolved in EtOH (20 mL) and N-hydroxyacetimidamide ((70.7 mg, 955 μmol) and zinc chloride ((130 mg, 955 μmol) were added. The reaction mixture was stirred at room temperature for 2 hours. HCl 37% (199 μl, 2.39 mmol) was added and the reaction mixture was warmed and stirred at 60° for 3 hours. The solvent was removed in vacuum. The residue was taken up with 25 mL sat. NaHCO$_3$ and extracted with CH$_2$Cl$_2$ (3×25 mL). The organic layers were dried over Na$_2$SO$_4$ and concentrated in vacuum. The crude material was purified by flash chromatography (silica gel, 0% to 10% MeOH in CH$_2$Cl$_2$, at the end 7M NH$_3$ in MeOH was used) to afford (1R,5S,8S)-3-(3-methyl-1,2,4-oxadiazol-5-yl)-3-azabicyclo[3.2.1]octan-8-amine as an off-white powder (126 mg, 76% yield). MS (ES+) m/z: 209.1 [(M+H)+].

General Procedure 1: Buchwald Coupling Reaction

To a solution of an intermediate 9, 15 or 20 in 1,4-dioxane was added 1.1 equivalent of an intermediate 10. The reaction mixture was degased and a palladium catalyst [either dibromo-bis-(tritert.-butyl)-phosphine-palladium (0.1 eq. CAS185812-86-6) or tri(dibenzylidenacetonne) dipalladium (0) CAS51364-51-3 in the presence of 2-di-tert-butylphosphino-2',4',6'-triisopropylbiphenyl CAS564483-19-8] and NaOtBu (2.1 eq.) were added. The reaction mixture was heated at 100° C. until completion of the reaction (usually between 2 and 8 hours) and concentrated under vacuo. A purification was done either by column chromatography or reverse phase preparative HPLC to afford the desired product.

EXAMPLE 1

4-(3,4-difluorophenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine

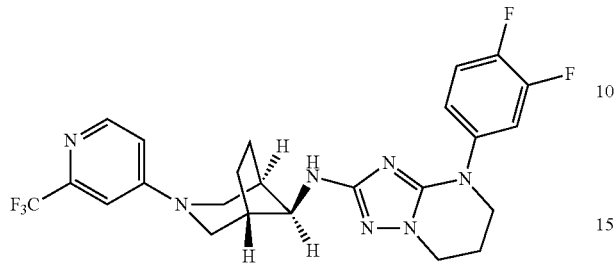

Using the general procedure 1, from 2-bromo-4-(3,4-difluorophenyl)-6,7-dihydro-5H-[1,2,4]triazolo[1,5-a]pyrimidine (15-1) and (1R,5S,8S)-3-[2-(trifluoromethyl)-4-pyridyl]-3-azabicyclo[3.2.1]octan-8-amine (10-5) was prepared 13 mg of the title compound as a white solid. MS (ES+) m/z: 506.2 [(M+H)$^+$].

EXAMPLE 2

N-[(1R,5S,8S)-3-(2-chloro-4-pyridyl)-3-azabicyclo[3.2.1]octan-8-yl]-4-(3,4-difluorophenyl)-6,7-dihydro-5H-[1,2,4]triazolo[1,5-a]pyrimidin-2-amine

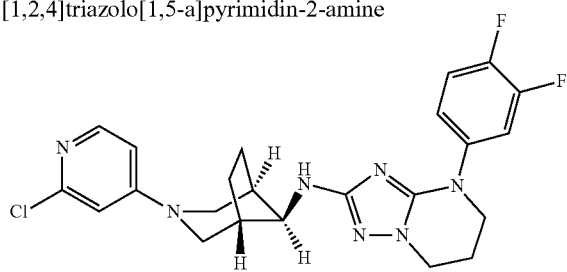

Using the general procedure 1, from 2-bromo-4-(3,4-difluorophenyl)-6,7-dihydro-5H-[1,2,4]triazolo[1,5-a]pyrimidine (15-1) and (1R,5S,8S)-3-(2-chloro-4-pyridyl)-3-azabicyclo[3.2.1]octan-8-amine (10-6) was prepared 15 mg of the title compound as a white solid. MS (ES+) m/z: 472.1 [(M+H)$^+$].

EXAMPLE 3

4-(3,4-difluorophenyl)-N-[(1R,5S,8S)-3-(6-methylpyrimidin-4-yl)-3-azabicyclo[3.2.1]octan-8-yl]-6,7-dihydro-5H-[1,2,4]triazolo[1,5-a]pyrimidin-2-amine

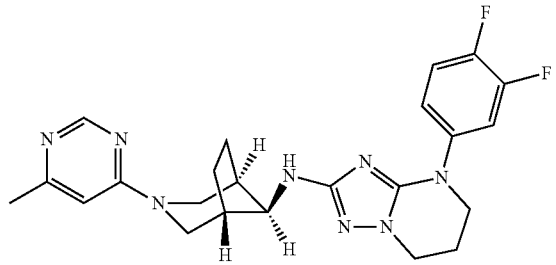 [SMILES: Cc1cc(N2C[C@H]3CC[C@@H](C2)[C@@H]3Nc2nc3n(n2)CCCN3c2ccc(F)c(F)c2)ncn1]

Using the general procedure 1, from 2-bromo-4-(3,4-difluorophenyl)-6,7-dihydro-5H-[1,2,4]triazolo[1,5-a]pyrimidine (15-1) and (1R,5S,8S)-3-(6-methylpyrimidin-4-yl)-3-azabicyclo[3.2.1]octan-8-amine (10-1) was prepared 26 mg of the title compound as a white solid. MS (ES+) m/z: 453.2 [(M+H)$^+$].

EXAMPLE 4

4-(3,4-difluorophenyl)-N-[(1R,5S,8S)-3-[2-(trifluoromethyl)-4-pyridyl]-3-azabicyclo[3.2.1]octan-8-yl]-5,6-dihydroimidazo[1,2-b][1,2,4]triazol-2-amine

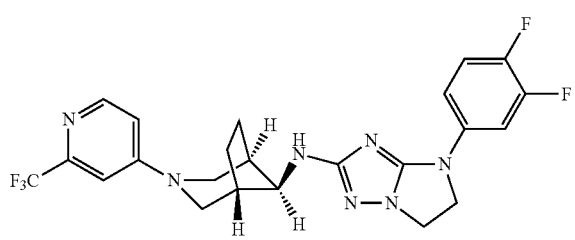 [SMILES: Fc1ccc(N2CCn3nc(N[C@@H]4[C@@H]5CC[C@H]4CN(c4ccnc(C(F)(F)F)c4)C5)nc32)cc1F]

Using the general procedure 1, from 2-bromo-4-(3,4-difluorophenyl)-5,6-dihydroimidazo[1,2-b][1,2,4]triazole (9-1) and (1R,5S,8S)-3-[2-(trifluoromethyl)-4-pyridyl]-3-azabicyclo[3.2.1]octan-8-amine (10-5) was prepared 40 mg of the title compound as a white solid. MS (ES+) m/z: 492.3 [(M+H)$^+$].

EXAMPLE 5

4-(3,4-difluorophenyl)-N-[(1R,5S,8S)-3-(6-methylpyrimidin-4-yl)-3-azabicyclo[3.2.1]octan-8-yl]-5,6-dihydroimidazo[1,2-b][1,2,4]triazol-2-amine

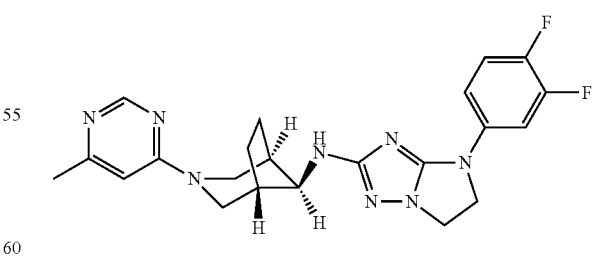

Using the general procedure 1, from 2-bromo-4-(3,4-difluorophenyl)-5,6-dihydroimidazo[1,2-b][1,2,4]triazole (9-1) and (1R,5S,8S)-3-(6-methylpyrimidin-4-yl)-3-azabicyclo[3.2.1]octan-8-amine (10-1) was prepared 24 mg of the title compound as a white solid. MS (ES+) m/z: 439.3 [(M+H)$^+$].

EXAMPLE 6

4-[4-(trifluoromethyl)phenyl]-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine

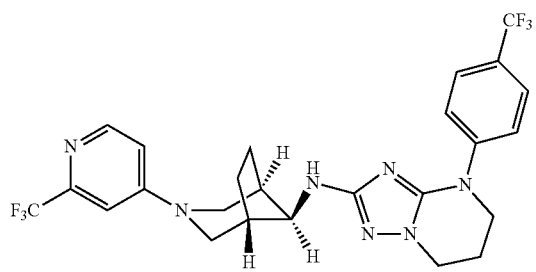 [SMILES: FC(F)(F)c1ccc(N2CCCn3nc(N[C@@H]4[C@@H]5CC[C@H]4CN(c4ccnc(C(F)(F)F)c4)C5)nc32)cc1]

Using the general procedure 1, from 2-bromo-4-[4-(trifluoromethyl)phenyl]-6,7-dihydro-5H-[1,2,4]triazolo[1,5-a]pyrimidine (15-2) and (1R,5S,8S)-3-[2-(trifluoromethyl)-4-pyridyl]-3-azabicyclo[3.2.1]octan-8-amine (10-5) was prepared 12 mg of the title compound as a white solid. MS (ES+) m/z: 538.2 [(M+H)$^+$].

EXAMPLE 7

4-[4-(trifluoromethyl)phenyl]-N-[(1R,5S,8S)-3-[2-(trifluoromethyl)-4-pyridyl]-3-azabicyclo[3.2.1]octan-8-yl]-5,6,7,8-tetrahydro-[1,2,4]triazolo[1,5-a][1,3]diazepin-2-amine

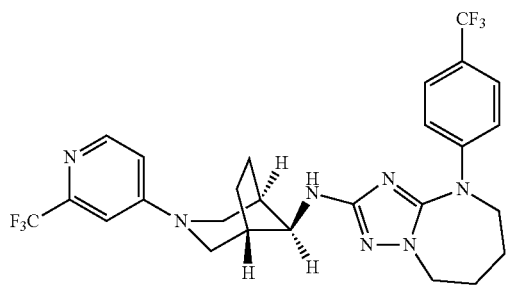 [SMILES: FC(F)(F)c1ccc(N2CCCCn3nc(N[C@@H]4[C@@H]5CC[C@H]4CN(c4ccnc(C(F)(F)F)c4)C5)nc32)cc1]

Using the general procedure 1, from 2-bromo-4-[4-(trifluoromethyl)phenyl]-5,6,7,8-tetrahydro-[1,2,4]triazolo[1,5-a][1,3]diazepine (20-2) and (1R,5S,8S)-3-[2-(trifluoromethyl)-4-pyridyl]-3-azabicyclo[3.2.1]octan-8-amine (10-5) was prepared 12 mg of the title compound as a white solid. MS (ES+) m/z: 552.2 [(M+H)$^+$].

EXAMPLE 8

N-[(1R,5S,8S)-3-(6-methylpyrimidin-4-yl)-3-azabicyclo[3.2.1]octan-8-yl]-4-[4-(trifluoromethyl)phenyl]-6,7-dihydro-5H-[1,2,4]triazolo[1,5-a]pyrimidin-2-amine

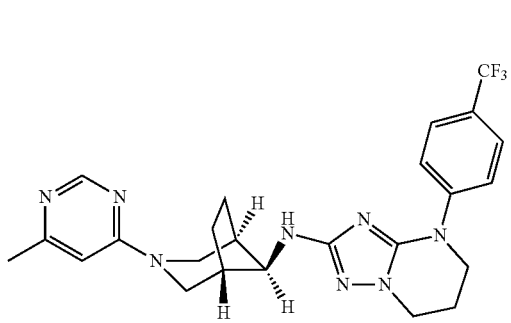 [SMILES: Cc1cc(N2C[C@H]3CC[C@@H](C2)[C@@H]3Nc2nc3n(n2)CCCN3c2ccc(C(F)(F)F)cc2)ncn1]

Using the general procedure 1, from 2-bromo-4-[4-(trifluoromethyl)phenyl]-6,7-dihydro-5H-[1,2,4]triazolo[1,5-a]pyrimidine (15-2) and (1R,5S,8S)-3-(6-methylpyrimidin-4-yl)-3-azabicyclo[3.2.1]octan-8-amine (10-1) was prepared 21 mg of the title compound as a white solid. MS (ES+) m/z: 484.2 [(M+H)$^+$].

EXAMPLE 9

N-[(1R,5S,8S)-3-(6-methylpyrimidin-4-yl)-3-azabicyclo[3.2.1]octan-8-yl]-4-[4-(trifluoromethyl)phenyl]-5,6,7,8-tetrahydro-[1,2,4]triazolo[1,5-a][1,3]diazepin-2-amine

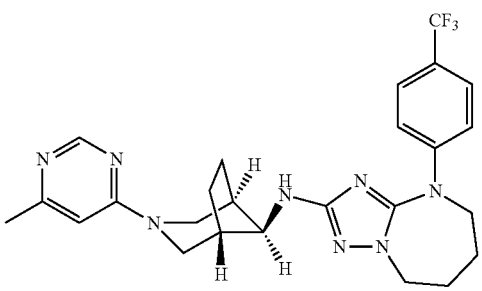 [SMILES: Cc1cc(N2C[C@H]3CC[C@@H](C2)[C@@H]3Nc2nc3n(n2)CCCCN3c2ccc(C(F)(F)F)cc2)ncn1]

Using the general procedure 1, from 2-bromo-4-[4-(trifluoromethyl)phenyl]-5,6,7,8-tetrahydro-[1,2,4]triazolo[1,5-a][1,3]diazepine (20-2) and (1R,5S,8S)-3-(6-methylpyrimidin-4-yl)-3-azabicyclo[3.2.1]octan-8-amine (10-1) was prepared 19 mg of the title compound as a white solid. MS (ES+) m/z: 499.2 [(M+H)$^+$].

EXAMPLE 10

4-(3-fluoro-4-methyl-phenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine

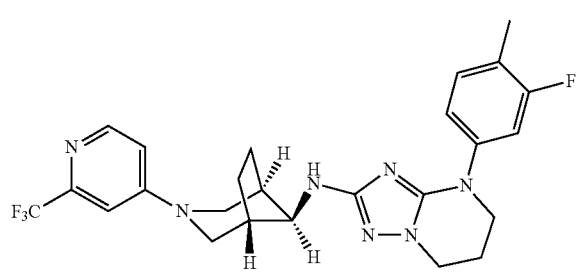 [SMILES: Cc1ccc(N2CCCn3nc(N[C@@H]4[C@@H]5CC[C@H]4CN(c4ccnc(C(F)(F)F)c4)C5)nc32)cc1F]

Using the general procedure 1, from 2-bromo-4-(3-fluoro-4-methyl-phenyl)-6,7-dihydro-5H-[1,2,4]triazolo[1,5-a]pyrimidine (15-4) and (1R,5S,8S)-3-[2-(trifluoromethyl)-4-pyridyl]-3-azabicyclo[3.2.1]octan-8-amine (10-5) was prepared 34 mg of the title compound as a white solid. MS (ES+) m/z: 502.2 [(M+H)+].

EXAMPLE 11

4-(3-fluoro-4-methyl-phenyl)-N-[(1R,5S,8S)-3-(6-methylpyrimidin-4-yl)-3-azabicyclo[3.2.1]octan-8-yl]-6,7-dihydro-5H-[1,2,4]triazolo[1,5-a]pyrimidin-2-amine

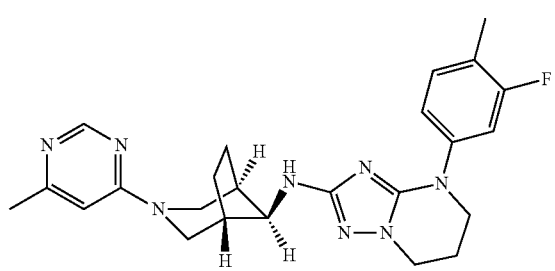 [SMILES: Cc1cc(N2C[C@H]3CC[C@@H](C2)[C@@H]3Nc2nc3n(n2)CCCN3c2ccc(C)c(F)c2)ncn1]

Using the general procedure 1, from 2-bromo-4-(3-fluoro-4-methyl-phenyl)-6,7-dihydro-5H-[1,2,4]triazolo[1,5-a]pyrimidine (15-4) and (1R,5S,8S)-3-(6-methylpyrimidin-4-yl)-3-azabicyclo[3.2.1]octan-8-amine (10-1) was prepared 29 mg of the title compound as a white solid. MS (ES+) m/z: 449.2 [(M+H)+].

EXAMPLE 12

N-[(1R,5S,8S)-3-(6-methylpyrimidin-4-yl)-3-azabicyclo[3.2.1]octan-8-yl]-4-[4-(trifluoromethyl)phenyl]-5,6-dihydroimidazo[1,2-b][1,2,4]triazol-2-amine

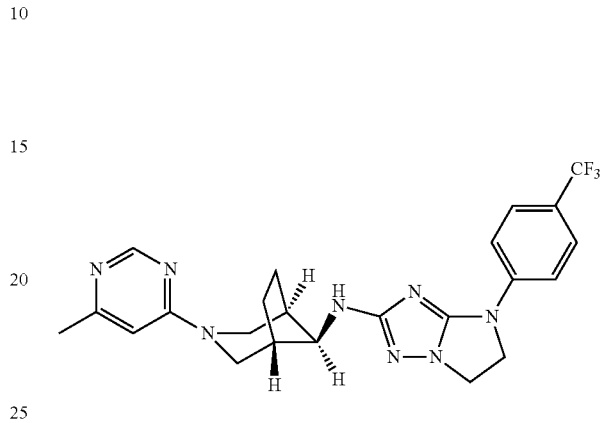

Using the general procedure 1, from 2-bromo-4-[4-(trifluoromethyl)phenyl]-5,6-dihydroimidazo [1,2-b][1,2,4]triazole (9-2) and (1R,5S,8S)-3-(6-methylpyrimidin-4-yl)-3-azabicyclo[3.2.1]octan-8-amine (10-1) was prepared 35 mg of the title compound as a white solid. MS (ES+) m/z: 471.3 [(M+H)+].

EXAMPLE 13

N-[(1R,5S,8S)-3-(6-chloropyrimidin-4-yl)-3-azabicyclo[3.2.1]octan-8-yl]-4-(3-fluoro-4-methyl-phenyl)-6,7-dihydro-5H-[1,2,4]triazolo[1,5-a]pyrimidin-2-amine

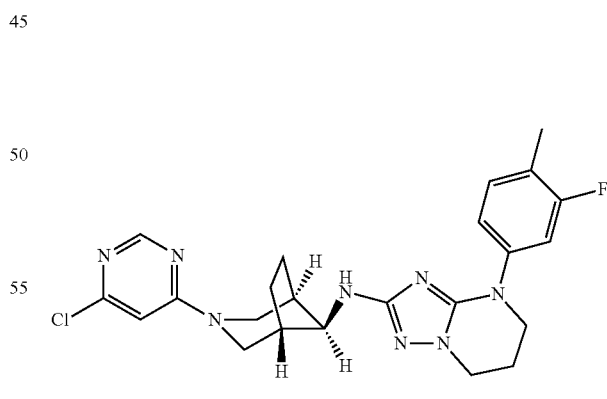

Using the general procedure 1, from 2-bromo-4-(3-fluoro-4-methyl-phenyl)-6,7-dihydro-5H-[1,2,4]triazolo[1,5-a]pyrimidine (15-4) and (1R,5S,8S)-3-(6-chloropyrimidin-4-yl)-3-azabicyclo[3.2.1]octan-8-amine (10-3) was prepared 4 mg of the title compound as a white solid. MS (ES+) m/z: 469.2 [(M+H)+].

EXAMPLE 14

4-(3,4-difluorophenyl)-N-[(1R,5S,8S)-3-(6-methoxypyrimidin-4-yl)-3-azabicyclo[3.2.1]octan-8-yl]-6,7-dihydro-5H-[1,2,4]triazolo[1,5-a]pyrimidin-2-amine

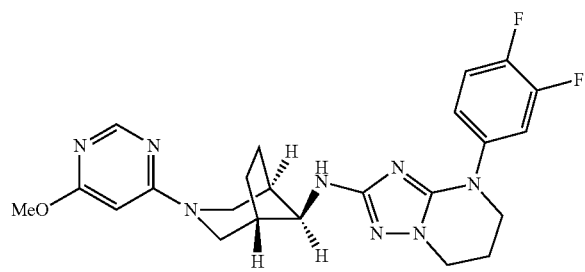 [SMILES: COc1cc(N2C[C@H]3CC[C@@H](C2)[C@@H]3Nc2nc3n(n2)CCCN3c2ccc(F)c(F)c2)ncn1]

Using the general procedure 1, from 2-bromo-4-(3,4-difluorophenyl)-6,7-dihydro-5H-[1,2,4]triazolo[1,5-a]pyrimidine (15-1) and (1R,5S,8S)-3-(6-methoxypyrimidin-4-yl)-3-azabicyclo[3.2.1]octan-8-amine (10-4) was prepared 29 mg of the title compound as a white solid. MS (ES+) m/z: 469.2 [(M+H)+].

EXAMPLE 15

4-(3,4-difluorophenyl)-N-[(1R,5S,8S)-3-(3-methyl-1,2,4-oxadiazol-5-yl)-3-azabicyclo[3.2.1]octan-8-yl]-6,7-dihydro-5H-[1,2,4]triazolo[1,5-a]pyrimidin-2-amine

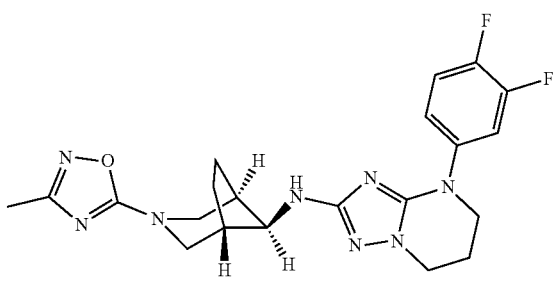 [SMILES: Cc1noc(N2C[C@H]3CC[C@@H](C2)[C@@H]3Nc2nc3n(n2)CCCN3c2ccc(F)c(F)c2)n1]

Using the general procedure 1, from 2-bromo-4-(3,4-difluorophenyl)-6,7-dihydro-5H-[1,2,4]triazolo[1,5-a]pyrimidine (15-1) and (1R,5S,8S)-3-(3-methyl-1,2,4-oxadiazol-5-yl)-3-azabicyclo[3.2.1]octan-8-amine (10-10) was prepared 16 mg of the title compound as a white solid. MS (ES+) m/z: 443.2 [(M+H)+].

EXAMPLE 16

N-[(1R,5S,8S)-3-(6-chloropyridazin-4-yl)-3-azabicyclo[3.2.1]octan-8-yl]-4-(3,4-difluorophenyl)-6,7-dihydro-5H-[1,2,4]triazolo[1,5-a]pyrimidin-2-amine

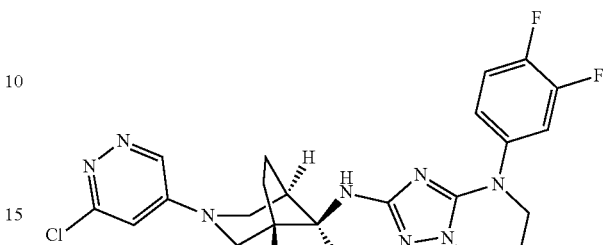

Using the general procedure 1, from 2-bromo-4-(3,4-difluorophenyl)-6,7-dihydro-5H-[1,2,4]triazolo[1,5-a]pyrimidine (15-1) and (1R,5S,8S)-3-(6-chloropyridazin-4-yl)-3-azabicyclo[3.2.1]octan-8-amine (10-8) was prepared 12 mg of the title compound as a white solid. MS (ES+) m/z: 473.1 [(M+H)+].

EXAMPLE 17

N-[(1R,5S,8S)-3-(6-chloropyrimidin-4-yl)-3-azabicyclo[3.2.1]octan-8-yl]-4-(3,4-difluorophenyl)-6,7-dihydro-5H-[1,2,4]triazolo[1,5-a]pyrimidin-2-amine

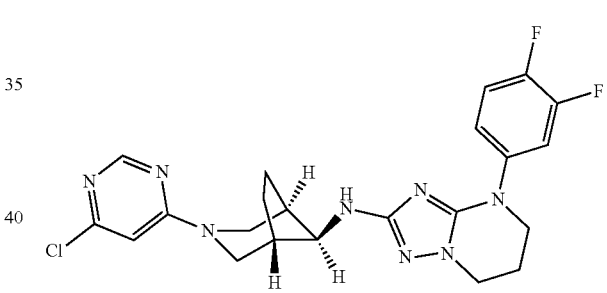

Using the general procedure 1, from 2-bromo-4-(3,4-difluorophenyl)-6,7-dihydro-5H-[1,2,4]triazolo[1,5-a]pyrimidine (15-1) and (1R,5S,8S)-3-(6-chloropyrimidin-4-yl)-3-azabicyclo[3.2.1]octan-8-amine (10-3) was prepared 4 mg of the title compound as a white solid. MS (ES+) m/z: 473.1 [(M+H)+].

EXAMPLE 18

4-(3,4-difluorophenyl)-N-[(1R,5S,8S)-3-(6-methoxypyridazin-4-yl)-3-azabicyclo[3.2.1]octan-8-yl]-6,7-dihydro-5H-[1,2,4]triazolo[1,5-a]pyrimidin-2-amine

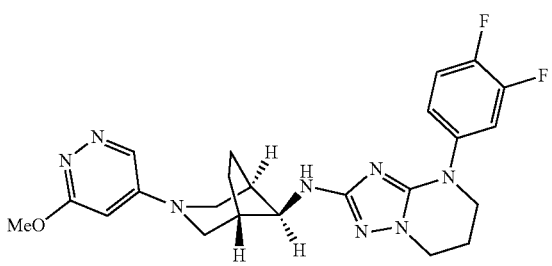 [SMILES: COc1cc(N2C[C@H]3CC[C@@H](C2)[C@@H]3Nc2nc3n(n2)CCCN3c2ccc(F)c(F)c2)cnn1]

Using the general procedure 1, from 2-bromo-4-(3,4-difluorophenyl)-6,7-dihydro-5H-[1,2,4]triazolo[1,5-a]pyrimidine (15-1) and (1R,5S,8S)-3-(6-methoxypyridazin-4-yl)-3-azabicyclo[3.2.1]octan-8-amine (10-9) was prepared 24 mg of the title compound as a white solid. MS (ES+) m/z: 469.2 [(M+H)+].

EXAMPLE 19

4-(3,4-difluorophenyl)-N-[(1R,5S,8S)-3-(5-fluoro-6-methyl-pyrimidin-4-yl)-3-azabicyclo[3.2.1]octan-8-yl]-6,7-dihydro-5H-[1,2,4]triazolo[1,5-a]pyrimidin-2-amine

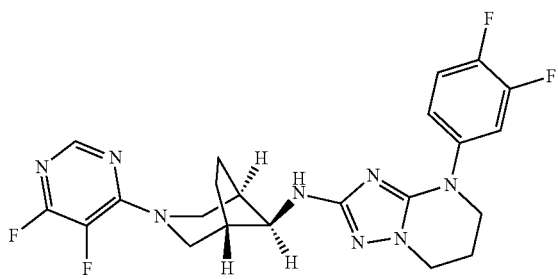 [SMILES: Fc1ccc(N2CCCn3nc(N[C@@H]4[C@@H]5CC[C@H]4CN(c4ncnc(F)c4F)C5)nc32)cc1F]

Using the general procedure 1, from 2-bromo-4-(3,4-difluorophenyl)-6,7-dihydro-5H-[1,2,4]triazolo[1,5-a]pyrimidine (15-1) and (1R,5S,8S)-3-(5-fluoro-6-methyl-pyrimidin-4-yl)-3-azabicyclo[3.2.1]octan-8-amine (10-2) was prepared 9 mg of the title compound as a white solid. MS (ES+) m/z: 471.2 [(M+H)+].

EXAMPLE 20

4-(3,4-difluorophenyl)-N-[(1R,5S,8S)-3-(6-methylpyridazin-4-yl)-3-azabicyclo[3.2.1]octan-8-yl]-6,7-dihydro-5H-[1,2,4]triazolo[1,5-a]pyrimidin-2-amine

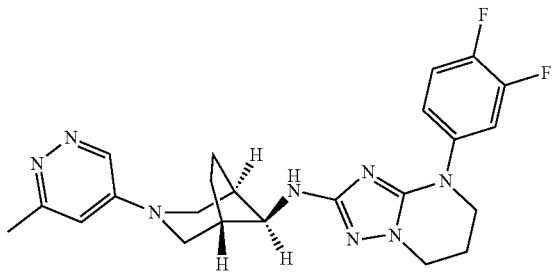 [SMILES: Cc1cc(N2C[C@H]3CC[C@@H](C2)[C@@H]3Nc2nc3n(n2)CCCN3c2ccc(F)c(F)c2)cnn1]

Step 1: Using the general procedure 1, from 2-bromo-4-(3,4-difluorophenyl)-6,7-dihydro-5H-[1,2,4]triazolo[1,5-a]pyrimidine (15-1) andtert-butyl(1R,5S,8S)-8-amino-3-azabicyclo[3.2.1]octane-3-carboxylate (commercially available) was prepared 130 mg of tert-butyl(1R,5S,8S)-8-[[4-(3,4-difluorophenyl)-6,7-dihydro-5H-[1,2,4]triazolo[1,5-a]pyrimidin-2-yl]amino]-3-azabicyclo[3.2.1]octane-3-carboxylate as a white solid. MS (ES+) m/z: 461.2 [(M+H)+].

Step 2: In analogy to the preparation of intermediate 10-1 (step 2) from tert-butyl(1R,5S,8S)-8-[[4-(3,4-difluorophenyl)-6,7-dihydro-5H-[1,2,4]triazolo[1,5-a]pyrimidin-2-yl]amino]-3-azabicyclo[3.2.1]octane-3-carboxylate (128 mg, 0.278 mmol) in CH2Cl2 in the presence of TFA (475 mg, 0.321 mL, 4.17 mmol), N-[(1R,5S,8S)-3-azabicyclo[3.2.1]octan-8-yl]-4-(3,4-difluorophenyl)-6,7-dihydro-5H-[1,2,4]triazolo[1,5-a]pyrimidin-2-amine (94 mg, 94%) was obtained as a light yellow oil and used directly in the next step without further purification. MS (ES+) m/z: 361.2 [(M+H)+].

Step 3: To a solution of N-[(1R,5S,8S)-3-azabicyclo[3.2.1]octan-8-yl]-4-(3,4-difluorophenyl)-6,7-dihydro-5H-[1,2,4]triazolo[1,5-a]pyrimidin-2-amine (30 mg, 0.083 mmol) in NMP (1 mL) was added 5-chloro-3-methylpyridazine (10.7 mg, 0.083 mmol) and DIPEA (32.3 mg, 43.6 µL, 0.25 mmol). The reaction mixture was heated at 110° C. for 4 hours, concentrated under vacuo before a purification by reverse phase preparative HPLC gave 4-(3,4-difluorophenyl)-N-[(1R,5S,8S)-3-(6-methylpyridazin-4-yl)-3-azabicyclo[3.2.1]octan-8-yl]-6,7-dihydro-5H-[1,2,4]triazolo[1,5-a]pyrimidin-2-amine (4 mg, 12%) as a white solid. MS (ES+) m/z: 453.2 [(M+H)+].

EXAMPLE 21

4-(3,4-difluorophenyl)-N-[(1R,5S,8S)-3-(2-methoxy-4-pyridyl)-3-azabicyclo[3.2.1]octan-8-yl]-6,7-dihydro-5H-[1,2,4]triazolo[1,5-a]pyrimidin-2-amine

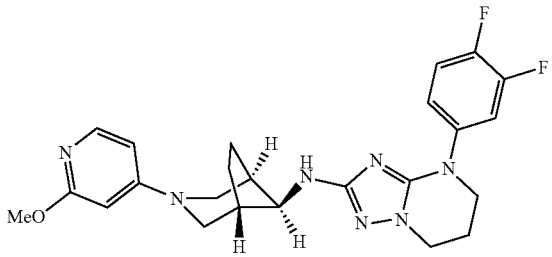 [SMILES: COc1cc(N2C[C@H]3CC[C@@H](C2)[C@@H]3Nc2nc3n(n2)CCCN3c2ccc(F)c(F)c2)ccn1]

Using the general procedure 1, from 2-bromo-4-(3,4-difluorophenyl)-6,7-dihydro-5H-[1,2,4]triazolo[1,5-a]pyrimidine (15-1) and (1R,5S,8S)-3-(2-methoxy-4-pyridyl)-3-azabicyclo [3.2.1]octan-8-amine (10-7) was prepared 7 mg of the title compound as a white solid. MS (ES+) m/z: 468.2 [(M+H)+].

EXAMPLE 22

4-(3,4-difluorophenyl)-N-[(1R,5S,8S)-3-[2-(trifluoromethyl)-4-pyridyl]-3-azabicyclo[3.2.1]octan-8-yl]-5,6,7,8-tetrahydro-[1,2,4]triazolo[1,5-a][1,3]diazepin-2-amine

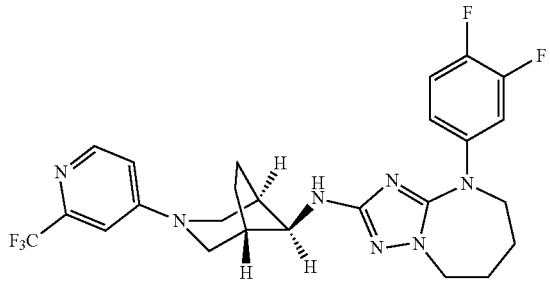 [SMILES: Fc1ccc(N2CCCCn3nc(N[C@@H]4[C@@H]5CC[C@H]4CN(c4ccnc(C(F)(F)F)c4)C5)nc32)cc1F]

Using the general procedure 1, from 2-bromo-4-(3,4-difluorophenyl)-5,6,7,8-tetrahydro-[1,2,4]triazolo[1,5-a][1,3]diazepine (20-1) and (1R,5S,8S)-3-[2-(trifluoromethyl)-4-pyridyl]-3-azabicyclo[3.2.1]octan-8-amine (10-5) was prepared 6 mg of the title compound as a white solid. MS (ES+) m/z: 520.2 [(M+H)+].

EXAMPLE 23

4-(3,4-difluorophenyl)-N-[(1R,5S,8S)-3-(6-methylpyrimidin-4-yl)-3-azabicyclo[3.2.1]octan-8-yl]-5,6,7,8-tetrahydro-[1,2,4]triazolo[1,5-a][1,3]diazepin-2-amine

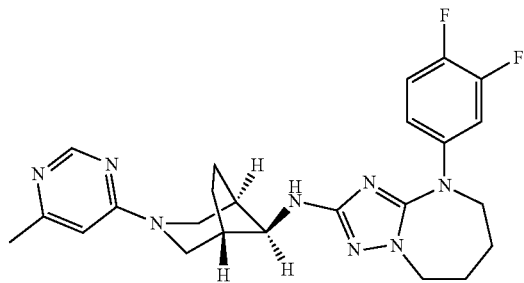 [SMILES: Cc1cc(N2C[C@H]3CC[C@@H](C2)[C@@H]3Nc2nc3n(n2)CCCCN3c2ccc(F)c(F)c2)ncn1]

Using the general procedure 1, from 2-bromo-4-(3,4-difluorophenyl)-5,6,7,8-tetrahydro-[1,2,4]triazolo[1,5-a][1,3]diazepine (20-1) and (1R,5S,8S)-3-(6-methylpyrimidin-4-yl)-3-azabicyclo[3.2.1]octan-8-amine (10-1) was prepared 12 mg of the title compound as a white solid. MS (ES+) m/z: 467.2 [(M+H)+].

EXAMPLE 24

4-(3,4-difluorophenyl)-N-[(1R,5S,8S)-3-(6-methoxypyrimidin-4-yl)-3-azabicyclo[3.2.1]octan-8-yl]-5,6,7,8-tetrahydro-[1,2,4]triazolo[1,5-a][1,3]diazepin-2-amine

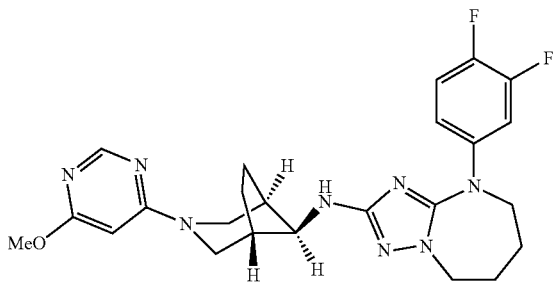 [SMILES: COc1cc(N2C[C@H]3CC[C@@H](C2)[C@@H]3Nc2nc3n(n2)CCCCN3c2ccc(F)c(F)c2)ncn1]

Using the general procedure 1, from 2-bromo-4-(3,4-difluorophenyl)-5,6,7,8-tetrahydro-[1,2,4]triazolo[1,5-a][1,3]diazepine (20-1) and (1R,5S,8S)-3-(6-methoxypyrimidin-4-yl)-3-azabicyclo[3.2.1]octan-8-amine (10-4) was prepared 7 mg of the title compound as a white solid. MS (ES+) m/z: 483.2 [(M+H)+].

EXAMPLE 25

N-[(1R,5S,8S)-3-(6-chloropyridazin-4-yl)-3-azabicyclo[3.2.1]octan-8-yl]-4-(3,4-difluorophenyl)-5,6,7,8-tetrahydro-[1,2,4]triazolo[1,5-a][1,3]diazepin-2-amine

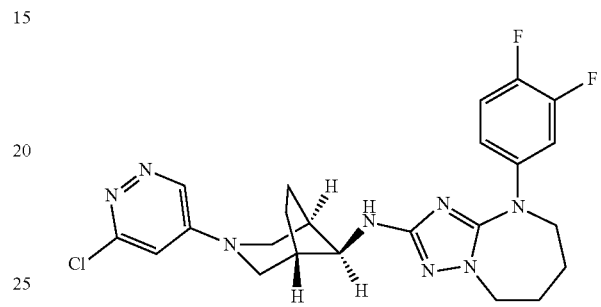

Using the general procedure 1, from 2-bromo-4-(3,4-difluorophenyl)-5,6,7,8-tetrahydro-[1,2,4]triazolo[1,5-a][1,3]diazepine (20-1) and (1R,5S,8S)-3-(6-chloropyridazin-4-yl)-3-azabicyclo[3.2.1]octan-8-amine (10-8) was prepared 4 mg of the title compound as a white solid. MS (ES+) m/z: 487.2 [(M+H)+].

EXAMPLE 26

4-(3,4-difluorophenyl)-N-[(1R,5S,8S)-3-(3-methyl-1,2,4-oxadiazol-5-yl)-3-azabicyclo[3.2.1]octan-8-yl]-5,6,7,8-tetrahydro-[1,2,4]triazolo[1,5-a][1,3]diazepin-2-amine

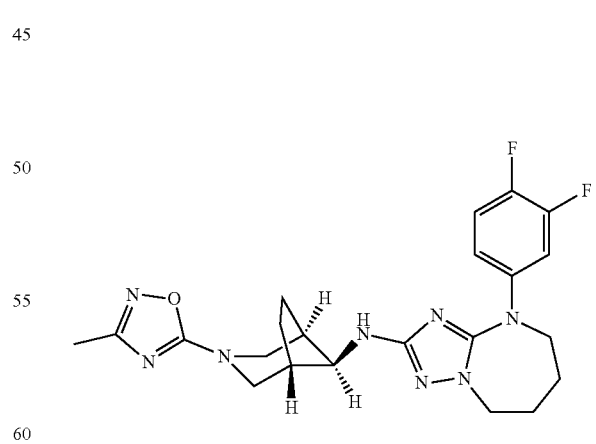

Using the general procedure 1, from 2-bromo-4-(3,4-difluorophenyl)-5,6,7,8-tetrahydro-[1,2,4]triazolo[1,5-a][1,3]diazepine (20-1) and (1R,5S,8S)-3-(3-methyl-1,2,4-oxadiazol-5-yl)-3-azabicyclo[3.2.1]octan-8-amine (10-10) was prepared 5 mg of the title compound as a white solid. MS (ES+) m/z: 457.2 [(M+H)+].

EXAMPLE 27

4-(3,4-difluorophenyl)-N-[(1R,5S,8S)-3-(6-methoxypyridazin-4-yl)-3-azabicyclo[3.2.1]octan-8-yl]-5,6,7,8-tetrahydro-[1,2,4]triazolo[1,5-a][1,3]diazepin-2-amine

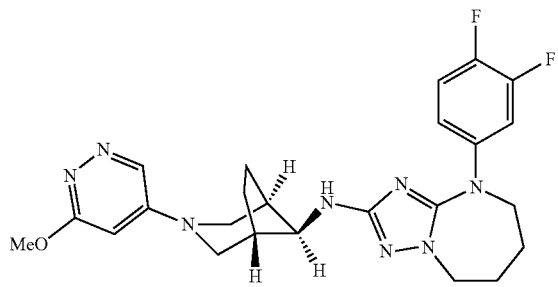 [SMILES: COc1cc(N2C[C@H]3CC[C@@H](C2)[C@@H]3Nc2nc3n(n2)CCCCN3c2ccc(F)c(F)c2)cnn1]

Using the general procedure 1, from 2-bromo-4-(3,4-difluorophenyl)-5,6,7,8-tetrahydro-[1,2,4]triazolo[1,5-a][1,3]diazepine (20-1) and (1R,5S,8S)-3-(6-methoxypyridazin-4-yl)-3-azabicyclo[3.2.1]octan-8-amine (10-9) was prepared 6 mg of the title compound as a white solid. MS (ES+) m/z: 483.2 [(M+H)$^+$].

EXAMPLE 28

4-(3,4-difluorophenyl)-N-[(1R,5S,8S)-3-(6-methylpyridazin-4-yl)-3-azabicyclo[3.2.1]octan-8-yl]-5,6,7,8-tetrahydro-[1,2,4]triazolo[1,5-a][1,3]diazepin-2-amine

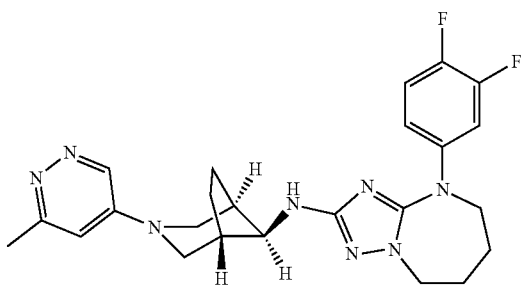 [SMILES: Cc1cc(N2C[C@H]3CC[C@@H](C2)[C@@H]3Nc2nc3n(n2)CCCCN3c2ccc(F)c(F)c2)cnn1]

In anlogy to example 20, from 2-bromo-4-(3,4-difluorophenyl)-5,6,7,8-tetrahydro-[1,2,4]triazolo[1,5-a][1,3]diazepine (20-1) was prepared 6 mg of the title compound as a white solid. MS (ES+) m/z: 467.2 [(M+H)$^+$].

EXAMPLE 29

N-[(1R,5S,8S)-3-[2-(trifluoromethyl)-4-pyridyl]-3-azabicyclo[3.2.1]octan-8-yl]-4-(2,3,4-trifluorophenyl)-6,7-dihydro-5H-[1,2,4]triazolo[1,5-a]pyrimidin-2-amine

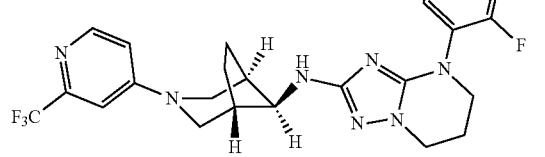

Using the general procedure 1, from 2-bromo-4-(2,3,4-trifluorophenyl)-6,7-dihydro-5H-[1,2,4]triazolo[1,5-a]pyrimidine (15-5) and (1R,5S,8S)-3-[2-(trifluoromethyl)-4-pyridyl]-3-azabicyclo[3.2.1]octan-8-amine (10-5) was prepared 22 mg of the title compound as a white solid. MS (ES+) m/z: 524.0 [(M+H)$^+$].

EXAMPLE 30

N-[(1R,5S,8S)-3-(6-methylpyrimidin-4-yl)-3-azabicyclo[3.2.1]octan-8-yl]-4-(2,3,4-trifluorophenyl)-6,7-dihydro-5H-[1,2,4]triazolo[1,5-a]pyrimidin-2-amine

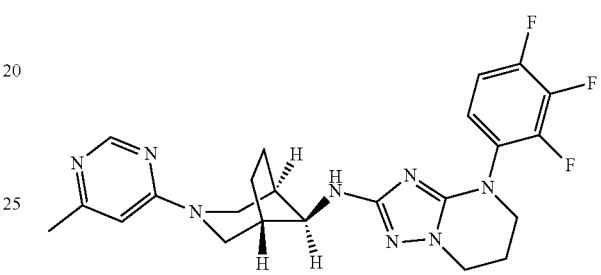

Using the general procedure 1, from 2-bromo-4-(2,3,4-trifluorophenyl)-6,7-dihydro-5H-[1,2,4]triazolo[1,5-a]pyrimidine (15-5) and (1R,5S,8S)-3-(6-methylpyrimidin-4-yl)-3-azabicyclo[3.2.1]octan-8-amine (10-1) was prepared 9 mg of the title compound as a white solid. MS (ES+) m/z: 471.2 [(M+H)$^+$].

EXAMPLE 31

N-[(1R,5S,8S)-3-(6-methoxypyrimidin-4-yl)-3-azabicyclo[3.2.1]octan-8-yl]-4-(2,3,4-trifluorophenyl)-6,7-dihydro-5H-[1,2,4]triazolo[1,5-a]pyrimidin-2-amine

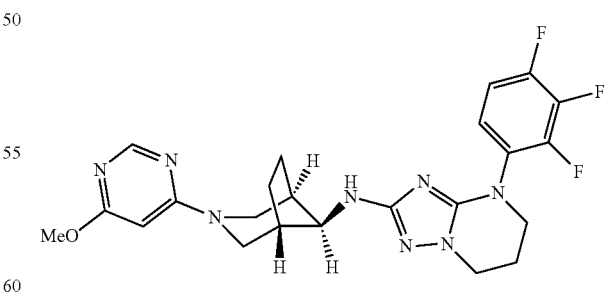

Using the general procedure 1, from 2-bromo-4-(2,3,4-trifluorophenyl)-6,7-dihydro-5H-[1,2,4]triazolo[1,5-a]pyrimidine (15-5) and (1R,5S,8S)-3-(6-methoxypyrimidin-4-yl)-3-azabicyclo[3.2.1]octan-8-amine (10-4) was prepared 10 mg of the title compound as a white solid. MS (ES+) m/z: 487.2 [(M+H)$^+$].

EXAMPLE 32

N-[(1R,5S,8S)-3-(6-chloropyridazin-4-yl)-3-azabicyclo[3.2.1]octan-8-yl]-4-(2,3,4-trifluorophenyl)-6,7-dihydro-5H-[1,2,4]triazolo[1,5-a]pyrimidin-2-amine

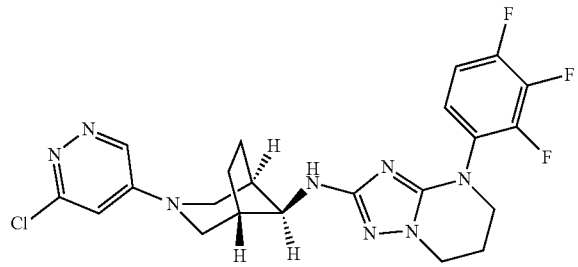 [SMILES: Fc1ccc(N2CCCn3nc(N[C@@H]4[C@@H]5CC[C@H]4CN(c4cnnc(Cl)c4)C5)nc32)c(F)c1F]

Using the general procedure 1, from 2-bromo-4-(2,3,4-trifluorophenyl)-6,7-dihydro-5H-[1,2,4]triazolo[1,5-a]pyrimidine (15-5) and (1R,5S,8S)-3-(6-chloropyridazin-4-yl)-3-azabicyclo[3.2.1]octan-8-amine (10-8) was prepared 22 mg of the title compound as a white solid. MS (ES+) m/z: 491.1 [(M+H)+].

EXAMPLE 33

N-[(1R,5S,8S)-3-(6-methoxypyridazin-4-yl)-3-azabicyclo[3.2.1]octan-8-yl]-4-(2,3,4-trifluorophenyl)-6,7-dihydro-5H-[1,2,4]triazolo[1,5-a]pyrimidin-2-amine

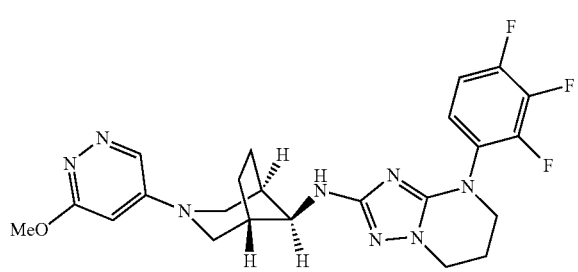 [SMILES: COc1cc(N2C[C@H]3CC[C@@H](C2)[C@@H]3Nc2nc3n(n2)CCCN3c2ccc(F)c(F)c2F)cnn1]

Using the general procedure 1, from 2-bromo-4-(2,3,4-trifluorophenyl)-6,7-dihydro-5H-[1,2,4]triazolo[1,5-a]pyrimidine (15-5) and (1R,5S,8S)-3-(6-methoxypyridazin-4-yl)-3-azabicyclo[3.2.1]octan-8-amine (10-9) was prepared 12 mg of the title compound as a white solid. MS (ES+) m/z: 487.2 [(M+H)+].

EXAMPLE 34

4-(3-fluorophenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine

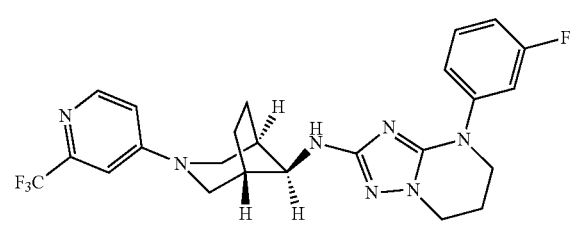 [SMILES: Fc1cccc(N2CCCn3nc(N[C@@H]4[C@@H]5CC[C@H]4CN(c4ccnc(C(F)(F)F)c4)C5)nc32)c1]

Using the general procedure 1, from 2-bromo-4-(3-fluorophenyl)-6,7-dihydro-5H-[1,2,4]triazolo[1,5-a]pyrimidine (15-6) and (1R,5S,8S)-3-[2-(trifluoromethyl)-4-pyridyl]-3-azabicyclo[3.2.1]octan-8-amine (10-5) was prepared 20 mg of the title compound as a white solid. MS (ES+) m/z: 488.2 [(M+H)+].

EXAMPLE 35

4-(3-fluorophenyl)-N-[(1R,5S,8S)-3-(6-methylpyrimidin-4-yl)-3-azabicyclo[3.2.1]octan-8-yl]-6,7-dihydro-5H-[1,2,4]triazolo[1,5-a]pyrimidin-2-amine

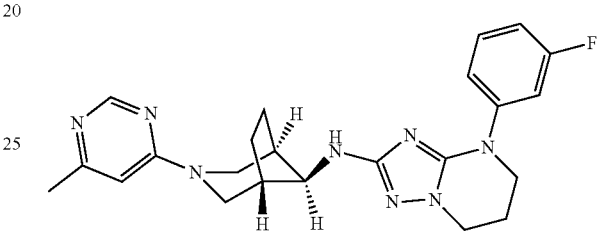

Using the general procedure 1, from 2-bromo-4-(3-fluorophenyl)-6,7-dihydro-5H-[1,2,4]triazolo[1,5-a]pyrimidine (15-6) and (1R,5S,8S)-3-(6-methylpyrimidin-4-yl)-3-azabicyclo[3.2.1]octan-8-amine (10-1) was prepared 14 mg of the title compound as a white solid. MS (ES+) m/z: 435.2 [(M+H)+].

EXAMPLE 36

4-(4-fluorophenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine

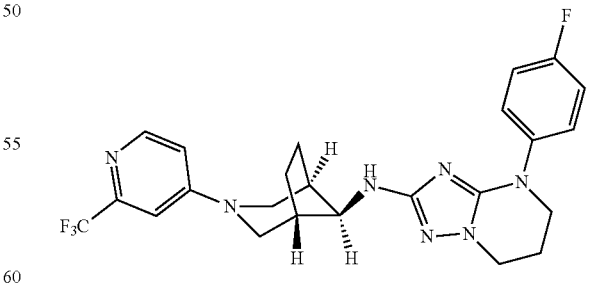

Using the general procedure 1, from 2-bromo-4-(4-fluorophenyl)-6,7-dihydro-5H-[1,2,4]triazolo[1,5-a]pyrimidine (15-7) and (1R,5S,8S)-3-[2-(trifluoromethyl)-4-pyridyl]-3-azabicyclo[3.2.1]octan-8-amine (10-5) was prepared 14 mg of the title compound as a white solid. MS (ES+) m/z: 488.2 [(M+H)+].

EXAMPLE 37

4-(4-fluorophenyl)-N-[(1R,5S,8S)-3-(6-methylpyrimidin-4-yl)-3-azabicyclo[3.2.1]octan-8-yl]-6,7-dihydro-5H-[1,2,4]triazolo[1,5-a]pyrimidin-2-amine

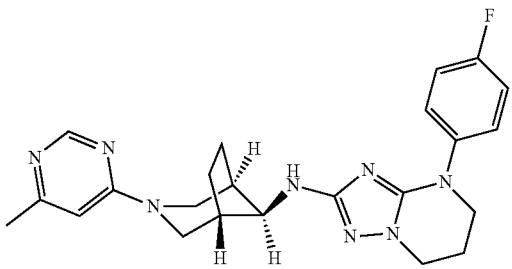 [SMILES: Cc1cc(N2C[C@H]3CC[C@@H](C2)[C@@H]3Nc2nc3n(n2)CCCN3c2ccc(F)cc2)ncn1]

Using the general procedure 1, from 2-bromo-4-(4-fluorophenyl)-6,7-dihydro-5H-[1,2,4]triazolo[1,5-a]pyrimidine (15-7) and (1R,5S,8S)-3-(6-methylpyrimidin-4-yl)-3-azabicyclo[3.2.1]octan-8-amine (10-1) was prepared 7 mg of the title compound as a white solid. MS (ES+) m/z: 435.2 [(M+H)$^+$].

EXAMPLE 38

4-(4-fluorophenyl)-N-[(1R,5S,8S)-3-(6-methoxypyrimidin-4-yl)-3-azabicyclo[3.2.1]octan-8-yl]-6,7-dihydro-5H-[1,2,4]triazolo[1,5-a]pyrimidin-2-amine

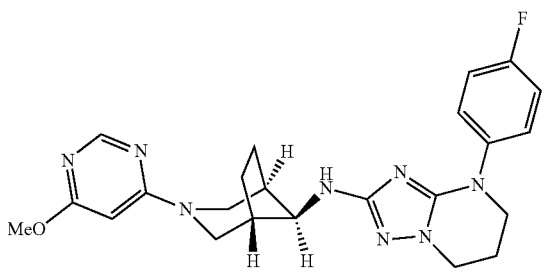 [SMILES: COc1cc(N2C[C@H]3CC[C@@H](C2)[C@@H]3Nc2nc3n(n2)CCCN3c2ccc(F)cc2)ncn1]

Using the general procedure 1, from 2-bromo-4-(4-fluorophenyl)-6,7-dihydro-5H-[1,2,4]triazolo[1,5-a]pyrimidine (15-7) and (1R,5S,8S)-3-(6-methoxypyrimidin-4-yl)-3-azabicyclo[3.2.1]octan-8-amine (10-4) was prepared 11 mg of the title compound as a white solid. MS (ES+) m/z: 451.3 [(M+H)$^+$].

EXAMPLE 39

4-(4-fluorophenyl)-N-[(1R,5S,8S)-3-(2-methoxy-4-pyridyl)-3-azabicyclo[3.2.1]octan-8-yl]-6,7-dihydro-5H-[1,2,4]triazolo[1,5-a]pyrimidin-2-amine

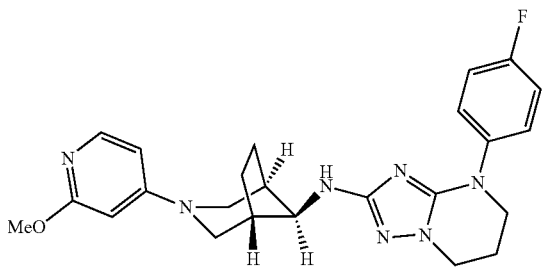 [SMILES: COc1cc(N2C[C@H]3CC[C@@H](C2)[C@@H]3Nc2nc3n(n2)CCCN3c2ccc(F)cc2)ccn1]

Using the general procedure 1, from 2-bromo-4-(4-fluorophenyl)-6,7-dihydro-5H-[1,2,4]triazolo[1,5-a]pyrimidine (15-7) and (1R,5S,8S)-3-(2-methoxy-4-pyridyl)-3-azabicyclo[3.2.1]octan-8-amine (10-7) was prepared 7 mg of the title compound as a white solid. MS (ES+) m/z: 450.2 [(M+H)$^+$].

EXAMPLE 40

4-(3,5-difluorophenyl)-N-[(1R,5S,8S)-3-(6-methylpyrimidin-4-yl)-3-azabicyclo[3.2.1]octan-8-yl]-6,7-dihydro-5H-[1,2,4]triazolo[1,5-a]pyrimidin-2-amine

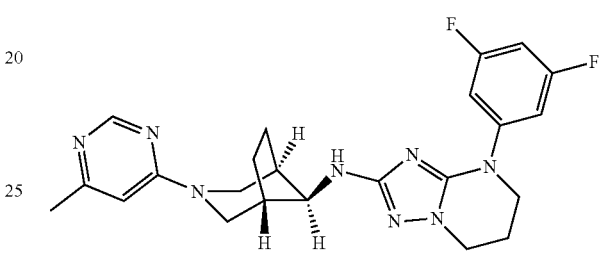

Using the general procedure 1, from 2-bromo-4-(3,5-difluorophenyl)-6,7-dihydro-5H-[1,2,4]triazolo[1,5-a]pyrimidine (15-3) and (1R,5S,8S)-3-(6-methylpyrimidin-4-yl)-3-azabicyclo[3.2.1]octan-8-amine (10-1) was prepared 7 mg of the title compound as a white solid. MS (ES+) m/z: 453.2 [(M+H)$^+$].

EXAMPLE 41

4-(3,5-difluorophenyl)-N-[1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine

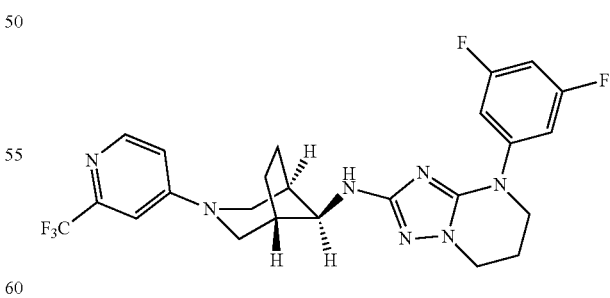

Using the general procedure 1, from 2-bromo-4-(3,5-difluorophenyl)-6,7-dihydro-5H-[1,2,4]triazolo[1,5-a]pyrimidine (15-3) and (1R,5S,8S)-3-[2-(trifluoromethyl)-4-pyridyl]-3-azabicyclo[3.2.1]octan-8-amine (10-5) was prepared 8 mg of the title compound as a white solid. MS (ES+) m/z: 506.2 [(M+H)$^+$].

EXAMPLE 42

4-(4-fluorophenyl)-N-[(1R,5S,8S)-3-(6-methoxy-pyridazin-4-yl)-3-azabicyclo[3.2.1]octan-8-yl]-6,7-dihydro-5H-[1,2,4]triazolo[1,5-a]pyrimidin-2-amine

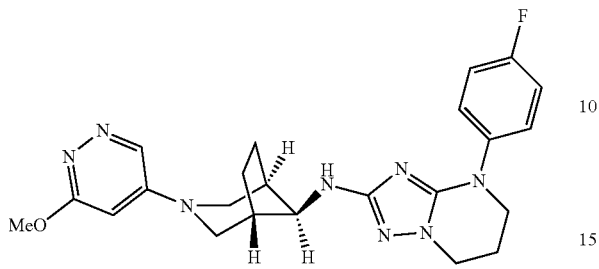

Using the general procedure 1, from 2-bromo-4-(4-fluorophenyl)-6,7-dihydro-5H-[1,2,4]triazolo[1,5-a]pyrimidine (15-7) and (1R,5S,8S)-3-(6-methoxypyridazin-4-yl)-3-azabicyclo[3.2.1]octan-8-amine (10-9) was prepared 9 mg of the title compound as a white solid. MS (ES+) m/z: 451.2 [(M+H)$^+$].

EXAMPLE 43

N-[(1R,5S,8S)-3-(5-fluoro-6-methyl-pyrimidin-4-yl)-3-azabicyclo[3.2.1]octan-8-yl]-4-(4-fluorophenyl)-6,7-dihydro-5H-[1,2,4]triazolo[1,5-a]pyrimidin-2-amine

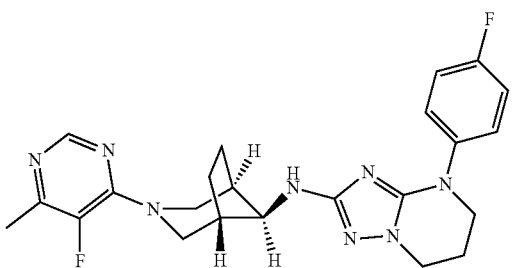 [SMILES: Cc1ncnc(N2C[C@H]3CC[C@@H](C2)[C@@H]3Nc2nc3n(n2)CCCN3c2ccc(F)cc2)c1F]

Using the general procedure 1, from 2-bromo-4-(4-fluorophenyl)-6,7-dihydro-5H-[1,2,4]triazolo[1,5-a]pyrimidine (15-7) and (1R,5S,8S)-3-(5-fluoro-6-methyl-pyrimidin-4-yl)-3-azabicyclo[3.2.1]octan-8-amine (10-2) was prepared 9 mg of the title compound as a white solid. MS (ES+) m/z: 453.2 [(M+H)$^+$].

EXAMPLE 44

4-(3-fluorophenyl)-N-[(1R,5S,8S)-3-(6-methoxy-pyridazin-4-yl)-3-azabicyclo[3.2.1]octan-8-yl]-6,7-dihydro-5H-[1,2,4]triazolo[1,5-a]pyrimidin-2-amine

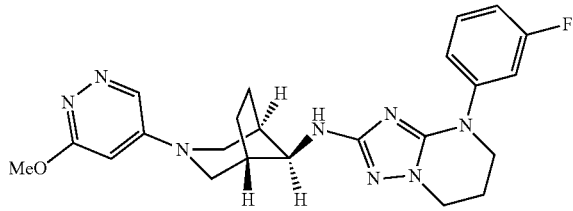 [SMILES: COc1cc(N2C[C@H]3CC[C@@H](C2)[C@@H]3Nc2nc3n(n2)CCCN3c2cccc(F)c2)cnn1]

Using the general procedure 1, from 2-bromo-4-(3-fluorophenyl)-6,7-dihydro-5H-[1,2,4]triazolo[1,5-a]pyrimidine (15-6) and (1R,5S,8S)-3-(6-chloropyridazin-4-yl)-3-azabicyclo[3.2.1]octan-8-amine (10-8) was prepared 12 mg of the title compound as a white solid. MS (ES+) m/z: 451.2 [(M+H)$^+$].

EXAMPLE 45

N-[(1R,5S,8S)-3-(5-fluoro-6-methyl-pyrimidin-4-yl)-3-azabicyclo[3.2.1]octan-8-yl]-4-(3-fluorophenyl)-6,7-dihydro-5H-[1,2,4]triazolo[1,5-a]pyrimidin-2-amine

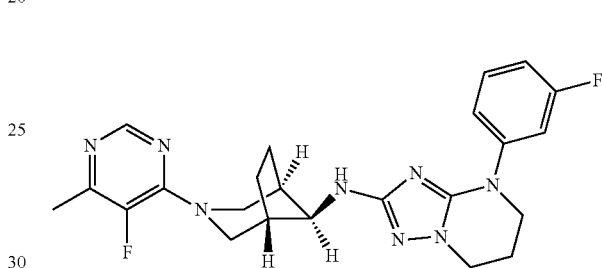

Using the general procedure 1, from 2-bromo-4-(3-fluorophenyl)-6,7-dihydro-5H-[1,2,4]triazolo[1,5-a]pyrimidine (15-6) and (1R,5S,8S)-3-(5-fluoro-6-methyl-pyrimidin-4-yl)-3-azabicyclo[3.2.1]octan-8-amine (10-2) was prepared 8 mg of the title compound as a white solid. MS (ES+) m/z: 453.2 [(M+H)$^+$].

EXAMPLE 46

4-(3-fluorophenyl)-N-[(1R,5S,8S)-3-(2-methoxy-4-pyridyl)-3-azabicyclo[3.2.1]octan-8-yl]-6,7-dihydro-5H-[1,2,4]triazolo[1,5-a]pyrimidin-2-amine

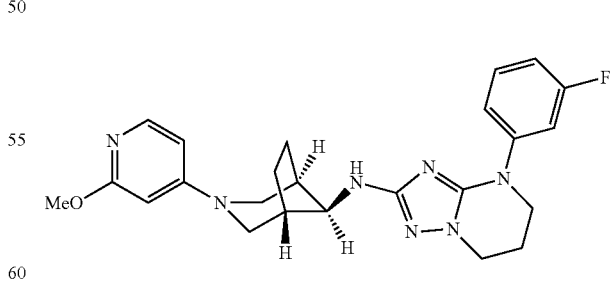

Using the general procedure 1, from 2-bromo-4-(3-fluorophenyl)-6,7-dihydro-5H-[1,2,4]triazolo[1,5-a]pyrimidine (15-6) and (1R,5S,8S)-3-(2-methoxy-4-pyridyl)-3-azabicyclo[3.2.1]octan-8-amine (10-7) was prepared 36 mg of the title compound as a white solid. MS (ES+) m/z: 450.2 [(M+H)$^+$].

EXAMPLE 47

4-(3-fluorophenyl)-N-[(1R,5S,8S)-3-(6-methoxypyrimidin-4-yl)-3-azabicyclo[3.2.1]octan-8-yl]-6,7-dihydro-5H-[1,2,4]triazolo[1,5-a]pyrimidin-2-amine

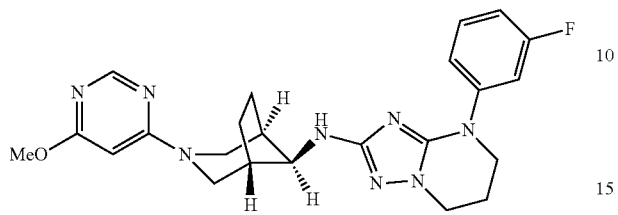

Using the general procedure 1, from 2-bromo-4-(3-fluorophenyl)-6,7-dihydro-5H-[1,2,4]triazolo[1,5-a]pyrimidine (15-6) and (1R,5S,8S)-3-(6-methoxypyrimidin-4-yl)-3-azabicyclo[3.2.1]octan-8-amine (10-4) was prepared 3 mg of the title compound as a white solid. MS (ES+) m/z: 451.2 [(M+H)$^+$].

EXAMPLE 48

N-[(1R,5S,8S)-3-(6-methylpyrimidin-4-yl)-3-azabicyclo[3.2.1]octan-8-yl]-4-(2,3,4-trifluorophenyl)-5,6-dihydroimidazo[1,2-b][1,2,4]triazol-2-amine

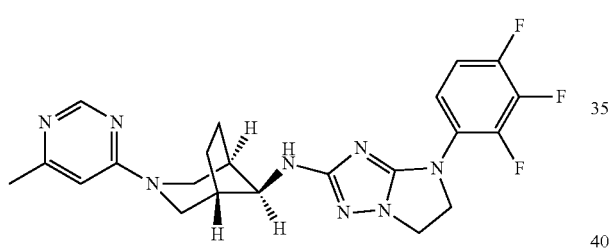

Using the general procedure 1, from 2-bromo-4-(2,3,4-trifluorophenyl)-5,6-dihydroimidazo[1,2-b][1,2,4]triazole (9-3) and (1R,5S,8S)-3-(6-methylpyrimidin-4-yl)-3-azabicyclo[3.2.1]octan-8-amine (10-1) was prepared 40 mg of the title compound as a white solid. MS (ES+) m/z: 457.3 [(M+H)$^+$].

EXAMPLE 49

4-(3,5-difluorophenyl)-N-[(1R,5S,8S)-3-(2-methoxy-4-pyridyl)-3-azabicyclo[3.2.1]octan-8-yl]-6,7-dihydro-5H-[1,2,4]triazolo[1,5-a]pyrimidin-2-amine

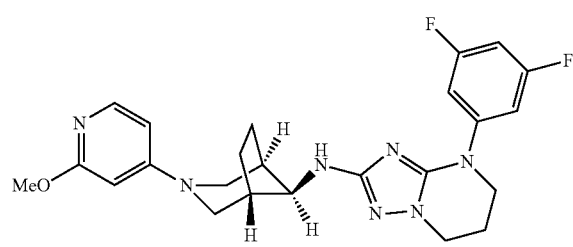 [SMILES: COc1cc(N2C[C@H]3CC[C@@H](C2)[C@@H]3Nc2nc3n(n2)CCCN3c2cc(F)cc(F)c2)ccn1]

Using the general procedure 1, from 2-bromo-4-(3,5-difluorophenyl)-6,7-dihydro-5H-[1,2,4]triazolo[1,5-a]pyrimidine (15-3) and (1R,5S,8S)-3-(2-methoxy-4-pyridyl)-3-azabicyclo[3.2.1]octan-8-amine (10-7) was prepared 6 mg of the title compound as a white solid. MS (ES+) m/z: 468.2 [(M+H)$^+$].

EXAMPLE 50

4-(4-methoxyphenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine

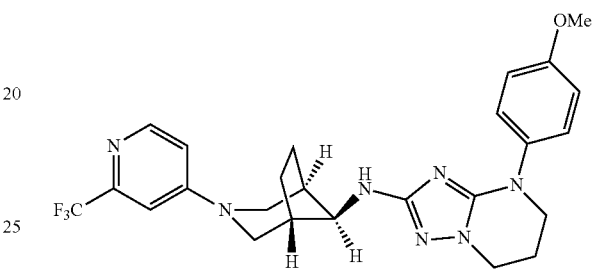

Using the general procedure 1, from 2-bromo-4-(4-methoxyphenyl)-6,7-dihydro-5H-[1,2,4]triazolo[1,5-a]pyrimidine (15-13) and (1R,5S,8S)-3-[2-(trifluoromethyl)-4-pyridyl]-3-azabicyclo[3.2.1]octan-8-amine (10-5) was prepared 48 mg of the title compound as a white solid. MS (ES+) m/z: 500.2 [(M+H)$^+$].

The invention claimed is:
1. A compound of formula I,

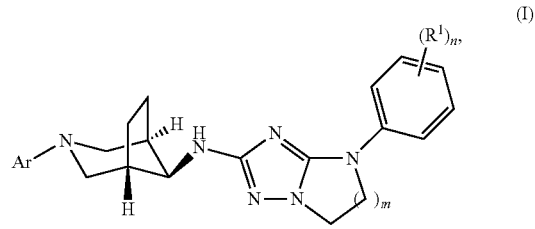

wherein:
each $R^1$ is independently hydrogen, halogen, lower alkyl, lower alkyl substituted by halogen, lower alkoxy, or lower alkoxy substituted by halogen;
n is 1, 2 or 3;
m is 1, 2 or 3;
Ar is a five or six membered heteroaryl group, selected from:

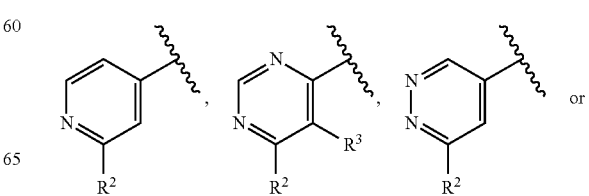

-continued

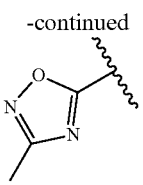

wherein:
R² is hydrogen, halogen, lower alkyl, lower alkyl substituted by halogen, or lower alkoxy;
R³ is hydrogen or halogen; and
—( )ₘ— is —(CH₂)ₘ—;
or a pharmaceutically active acid addition salt thereof.

2. A compound of formula I-1

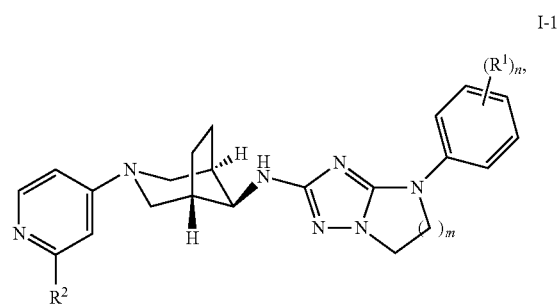

wherein:
each R¹ is independently hydrogen, halogen, lower alkyl, lower alkyl substituted by halogen, lower alkoxy or lower alkoxy substituted by halogen;
n is 1, 2 or 3;
m is 1, 2 or 3;
R² is hydrogen, halogen, lower alkyl, lower alkyl substituted by halogen, or lower alkoxy; and
—( )ₘ— is —(CH₂)ₘ—;
or a pharmaceutically active acid addition salt thereof.

3. A compound of formula I-1 according to claim 2, selected from:
4-(3,4-difluorophenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine;
N-[(1R,5 S,8S)-3-(2-chloro-4-pyridyl)-3-azabicyclo[3.2.1]octan-8-yl]-4-(3,4-difluorophenyl)-6,7-dihydro-5H-[1,2,4]triazolo[1,5-a]pyrimidin-2-amine;
4-(3,4-difluorophenyl)-N-[(1R,5S,8S)-3-[(trifluoromethyl)-4-pyridyl]-3-azabicyclo[3.2.1]octan-8-yl]-5,6-dihydroimidazo[1,2-b][1,2,4]triazol-2-amine;
4-[4-(trifluoromethyl)phenyl]-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine;
4-[4-(trifluoromethyl)phenyl]-N-[(1R,5S,8S)-3-[2-(trifluoromethyl)-4-pyridyl]-3-azabicyclo[3.2.1]octan-8-yl]-5,6,7,8-tetrahydro-[1,2,4]triazolo[1,5-a][1,3]diazepin-2-amine;
4-(3-fluoro-4-methyl-phenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine;
4-(3,4-difluorophenyl)-N-[(1R,5S,8S)-3-(2-methoxy-4-pyridyl)-3-azabicyclo[3.2.1]octan-8-yl]-6,7-dihydro-5H[1,2,4]triazolo[1,5-a]pyrimidin-2-amine;
4-(3,4-difluorophenyl)-N-[(1R,5S,8S)-3-[2-(trifluoromethyl)-4-pyridyl]-3-azabicyclo[3.2.1]octan-8-yl]-5,6,7,8-tetrahydro-[1,2,4]triazolo[1,5-a][1,3]diazepin-2-amine;
N-[1R,5S,8S)-3-[2-(trifluoromethyl)-4-pyridyl]-3-azabicyclo[3.2.1]octan-8-yl]-4-(2,3,4-trifluorophenyl)-6,7-dihydro-5H-[1,2,4]triazolo[1,5-a]pyrimidin-2-amine;
4-(3-fluorophenyl)-N-[(1R,5S,8S)-3-[2(trifluoromethyl)-4-pyridyl]-3-azabicyclo[3.2.1]octan-8-yl]-6,7-dihydro-5H-[1,2,4]triazolo[1,5-a]pyrimidin-2-amine;
4-(4-fluorophenyl)-N-[(1R,5S,8S)-3-[2(trifluoromethyl)-4-pyridyl]-3-azabicyclo[3.2.1]octan-8-yl]-6,7-dihydro-5H-[1,2,4]triazolo[1,5-a]pyrimidin-2-amine;
4-(4-fluorophenyl)-N-[(1R,5S,8S)-3-(2-methoxy-4-pyridyl)-3-azabicyclo[3.2.1]octan-8-yl]-6,7-dihydro-5H-[1,2,4]triazolo[1,5-a]pyrimidin-2-amine;
4-(3,5-difluorophenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine;
4-(3-fluorophenyl)-N-[(1R,5S,8S)-3-(2-methoxy-4-pyridyl)-3-azabicyclo[3.2.1]octan-8-yl]-6,7-dihydro-5H-[1,2,4]triazolo[1,5-a]pyrimidin-2-amine;
4-(3,5-difluorophenyl)-N-[(1R,5S,8S)-3-(2-methoxy-4-pyridyl)-3-azabicyclo[3.2.1]octan-8-yl]-6,7-dihydro-5H-[1,2,4]triazolo[1,5-a]pyrimidin-2-amine; and 4-(4-methoxyphenyl)-N-[(1R,5S,8S)-3-[2-(trifluoromethyl)-4-pyridyl]-3-azabicyclo[3.2.1]octan-8-yl]-6,7-dihydro-5H-[1,2,4]triazolo[1,5-a]pyrimidin-2-amine, or a pharmaceutically active acid addition salt thereof.

4. A compound of formula I-2,

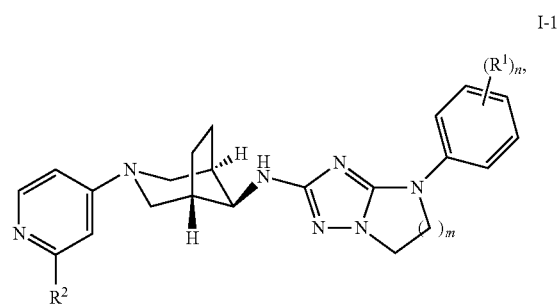

wherein:
each R¹ is independently hydrogen, halogen, lower alkyl, lower alkyl substituted by halogen, lower alkoxy or lower alkoxy substituted by halogen;
n is 1, 2 or 3;
m is 1, 2 or 3;
R² is hydrogen, halogen, lower alkyl, lower alkyl substituted by halogen, or lower alkoxy;
R³ is hydrogen or halogen; and
—( )ₘ— is —(CH₂)ₘ—;
or a pharmaceutically active acid addition salt thereof.

5. A compound of formula I-2 according to claim 4, selected from the group consisting of:
4-(3,4-difluorophenyl)-N-[(1R,5S,8S)-3-(6-methylpyrimidin-4-yl)-3-azabicyclo[3.2.1]octan-8-yl]-6,7-dihydro-5H-[1,2,4]triazolo[1,5-a]pyrimidin-2-amine;
4-(3,4-difluorophenyl)-N-[(1R,5S,8S)-3-(6-methylpyrimidin-4-yl)-3-azabicyclo[3.2.1]octan-8-yl]-5,6-dihydroimidazo[1,2-b][1,2,4]triazol-2-amine;

N-[(1R,5 S,8S)-3-(6-methylpyrimidin-4-yl)-3-azabicyclo[3.2.1]octan-8-yl]-4-[4-(trifluoromethyl)phenyl]-6,7-dihydro-5H-[1,2,4]triazolo[1,5-a]pyrimidin-2-amine;

N-[(1R,5 S,8S)-3-(6-methylpyrimidin-4-yl)-3-azabicyclo[3.2.1]octan-8-yl]-4-[4-(trifluoromethyl)phenyl]-5,6,7,8-tetrahydro-[1,2,4]triazolo[1,5-a][1,3]diazepin-2-amine;

4-(3-fluoro-4-methyl-phenyl)-N-[(1R,5 S,8S)-3-(6-methylpyrimidin-4-yl)-3-azabicyclo[3.2.1]octan-8-yl]-6,7-dihydro-5H-[1,2,4]triazolo[1,5-a]pyrimidin-2-amine;

N-[1R, 5 S,8S)-3-(6-methylpyrimidin-4-yl)-3-azabicyclo[3.2.1]octan-8-yl]-4-[4-(trifluoromethyl)phenyl]-5,6-dihydroimidazo[1,2-b][1,2,4]triazol-2-amine;

N-[(1R,5 S,8S)-3-(6-chloropyrimidin-4-yl)-3-azabicyclo[3.2.1]octan-8-yl]-4-(3-fluoro-4-methyl-phenyl)-6,7-dihydro-5H-[1,2,4]triazolo[1,5-a]pyrimidin-2-amine;

4-(3,4-difluorophenyl)-N-[(1R,5 S,8S)-3-(6-methoxypyrimidin-4-yl)-3-azabicyclo[3.2.1]octan-8-yl]-6,7-dihydro-5H-[1,2,4]triazolo[1,5-a]pyrimidin-2-amine;

N-[(1R,5 S,8S)-3-(6-chloropyrimidin-4-yl)-3-azabicyclo[3.2.1]octan-8-yl]-4-(3,4-difluorophenyl)-6,7-dihydro-5H-[1,2,4]triazolo[1,5-a]pyrimidin-2-amine;

4-(3,4-difluorophenyl)-N-[(1R,5 S,8S)-3-(5-fluoro-6-methyl-pyrimidin-4-yl)-3-azabicyclo[3.2.1]octan-8-yl]-6,7-dihydro-5H-[1,2,4]triazolo[1,5-a]pyrimidin-2-amine;

4-(3,4-difluorophenyl)-N-[(1R,5 S,8S)-3-(6-methylpyrimidin-4-yl)-3-azabicyclo[3.2.1]octan-8-yl]-5,6,7,8-tetrahydro-[1,2,4]triazolo[1,5-a][1,3]diazepin-2-amine;

4-(3,4-difluorophenyl)-N-[(1R,5 S,8S)-3-(6-methoxypyrimidin-4-yl)-3-azabicyclo[3.2.1]octan-8-yl]-5,6,7,8-tetrahydro-[1,2,4]triazolo[1,5-a][1,3]diazepin-2-amine;

N-[(1R,5 S,8S)-3-(6-methylpyrimidin-4-yl)-3-azabicyclo[3.2.1]octan-8-yl]-4-(2,3,4-trifluorophenyl)-6,7-dihydro-5H-[1,2,4]triazolo[1,5-a]pyrimidin-2-amine;

N-[(1R,5 S,8S)-3-(6-methoxypyrimidin-4-yl)-3-azabicyclo[3.2.1]octan-8-yl]-4-(2,3,4-trifluorophenyl)-6,7-dihydro-5H-[1,2,4]triazolo[1,5-a]pyrimidin-2-amine;

4-(3-fluorophenyl)-N-[(1R,5 S, 8 S)-3-(6-methylpyrimidin-4-yl)-3-azabicyclo[3.2.1]octan-8-yl]-6,7-dihydro-5H-[1,2,4]triazolo[1,5-a]pyrimidin-2-amine;

4-(4-fluorophenyl)-N-[(1R,5 S, 8 S)-3-(6-methylpyrimidin-4-yl)-3-azabicyclo[3.2.1]octan-8-yl]-6,7-dihydro-5H-[1,2,4]triazolo[1,5-a]pyrimidin-2-amine;

4-(4-fluorophenyl)-N-[(1R,5 S, 8 S)-3-(6-methoxypyrimidin-4-yl)-3-azabicyclo[3.2.1]octan-8-yl]-6,7-dihydro-5H-[1,2,4]triazolo[1,5-a]pyrimidin-2-amine;

4-(3,5-difluorophenyl)-N-[(1R,5 S,8S)-3-(6-methylpyrimidin-4-yl)-3-azabicyclo[3.2.1]octan-8-yl]-6,7-dihydro-5H-[1,2,4]triazolo[1,5-a]pyrimidin-2-amine;

N-[(1R,5S,8S)-3-(5-fluoro-6-methyl-pyrimidin-4-yl)-3-azabicyclo[3.2.1]octan-8-yl]-4-(4-fluorophenyl)-6,7-dihydro-5H-[1,2,4]triazolo[1,5-a]pyrimidin-2-amine;

N-[(1R,5S,8S)-3-(5-fluoro-6-methyl-pyrimidin-4-yl)-3-azabicyclo[3.2.1]octan-8-yl]-4-(3-fluorophenyl)-6,7-dihydro-5H-[1,2,4]triazolo[1,5-a]pyrimidin-2-amine;

4-(3-fluorophenyl)-N-[(1R,5S,8S)-3-(6-methoxypyrimidin-4-yl)-3-azabicyclo[3.2.1]octan-8-yl]-6,7-dihydro-5H-[1,2,4]triazolo[1,5-a]pyrimidin-2-amine; and N-[(1R,5S,8S)-3-(6-methylpyrimidin-4-yl)-3-azabicyclo[3.2.1]octan-8-yl]-4-(2,3,4-trifluorophenyl)-5,6-dihydroimidazo[1,2-b][1,2,4]triazol-2-amine, or a pharmaceutically active acid addition salt thereof.

6. A compound of formula I-3

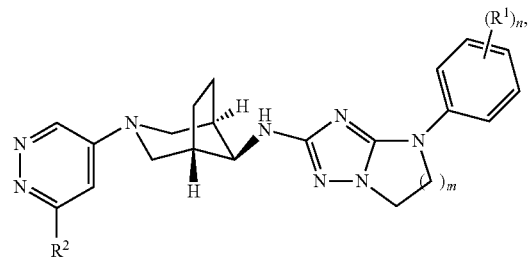

I-3 wherein:
each $R^1$ is independently hydrogen, halogen, lower alkyl, lower alkyl substituted by halogen, lower alkoxy or lower alkoxy substituted by halogen;
n is 1, 2 or 3;
m is 1, 2 or 3;
$R^2$ is hydrogen, halogen, lower alkyl, lower alkyl substituted by halogen, or lower alkoxy;
and
—( )$_m$— is —(CH$_2$)$_m$—;
or a pharmaceutically active acid addition salt thereof.

7. A compound of formula I-3 according to claim 6, selected from:

N-[(1R,5 S, 8 S)-3-(6-chloropyridazin-4-yl)-3-azabicyclo[3.2.1]octan-8-yl]-4-(3,4-difluorophenyl)-6,7-dihydro-5H-[1,2,4]triazolo[1,5-a]pyrimidin-2-amine;

4-(3,4-difluorophenyl)-N-[(1R,5 S, 8 S)-3-(6-methoxypyridazin-4-yl)-3-azabicyclo[3.2.1]octan-8-yl]-6,7-dihydro-5H-[1,2,4]triazolo[1,5-a]pyrimidin-2-amine;

4-(3,4-difluorophenyl)-N-[(1R,5 S, 8 S)-3-(6-methylpyridazin-4-yl)-3-azabicyclo[3.2.1]octan-8-yl]-6,7-dihydro-5H-[1,2,4]triazolo[1,5-a]pyrimidin-2-amine;

N-[(1R,5S,8S)-3-(6-chloropyridazin-4-yl)-3-azabicyclo[3.2.1]octan-8-yl]-4-(3,4-difluorophenyl)-5,6,7,8-tetrahydro-[1,2,4]triazolo[1,5-a][1,3]diazepin-2-amine;

4-(3,4-difluorophenyl)-N-[(1R,5S,8S)-3-(6-methoxypyridazin-4-yl)-3-azabicyclo[3.2.1]octan-8-yl]-5,6,7,8-tetrahydro-[1,2,4]triazolo[1,5-a][1,3]diazepin-2-amine;

4-(3,4-difluorophenyl)-N-[(1R,5S,8S)-3-(6-methylpyridazin-4-yl)-3-azabicyclo[3.2.1]octan-8-yl]-5,6,7,8-tetrahydro-[1,2,4]triazolo[1,5-a][1,3]diazepin-2-amine;

N-[(1R,5S,8S)-3-(6-chloropyridazin-4-yl)-3-azabicyclo[3.2.1]octan-8-yl]-4-(2,3,4-trifluorophenyl)-6,7-dihydro-5H-[1,2,4]triazolo[1,5-a]pyrimidin-2-amine;

N-[(1R,5S,8S)-3-(6-methoxypyridazin-4-yl)-3-azabicyclo[3.2.1]octan-8-yl]-4-(2,3,4-trifluorophenyl)-6,7-dihydro-5H-[1,2,4]triazolo[1,5-a]pyrimidin-2-amine;

4-(4-fluorophenyl)-N-[(1R,5S,8S)-3-(6-methoxypyridazin-4-yl)-3-azabicyclo[3.2.1]octan-8-yl]-6,7-dihydro-5H-[1,2,4]triazolo[1,5-a]pyrimidin-2-amine; and 4-(3-fluorophenyl)-N-[(1R,5S,8S)-3-(6-methoxypyridazin-4-yl)-3-azabicyclo[3.2.1]octan-8-yl]-6,7-dihydro-5H-[1,2,4]triazolo[1,5-a]pyrimidin-2-amine, or a pharmaceutically active acid addition salt thereof.

8. A compound of formula I-4,

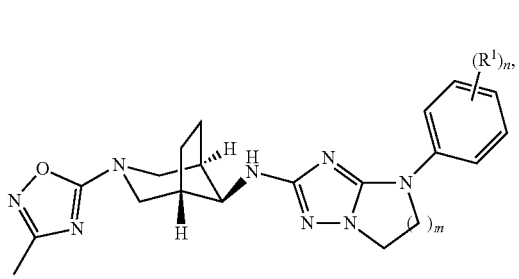

wherein:
each $R^1$ is independently hydrogen, halogen, lower alkyl, lower alkyl substituted by halogen, lower alkoxy or lower alkoxy substituted by halogen;
n is 1, 2 or 3;
m is 1, 2 or 3; and
—( )$_m$— is —(CH$_2$)$_m$—;
or a pharmaceutically active acid addition salt thereof.

9. A compound of formula I-4 according to claim 8, selected from:
4-(3,4-difluorophenyl)-N-[(1R,5S,8S)-3-(3-methyl-1,2,4-oxadiazol-5-yl)-3-azabicyclo[3.2.1]octan-8-yl]-6,7-dihydro-5H-[1,2,4]triazolo[1,5-a]pyrimidin-2-amine; and
4-(3,4-difluorophenyl)-N-[(1R,5 S, 8 S)-3-(3-methyl-1,2,4-oxadiazol-5-yl)-3-azabicyclo[3.2.1]octan-8-yl]-5,6,7,8-tetrahydro-[1,2,4]triazolo[1,5-a][1,3]diazepin-2-amine, or a pharmaceutically active acid addition salt thereof.

10. A process for preparing a compound of formula I, which process comprises:
a) reacting a compound of formula 9

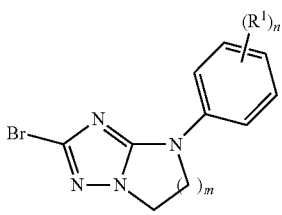

with a compound of formula 10

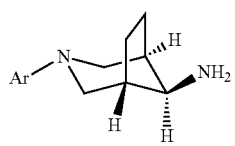

to form a compound of formula I

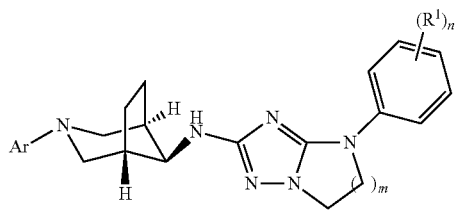

wherein:
each $R^1$ is independently hydrogen, halogen, lower alkyl, lower alkyl substituted by halogen, lower alkoxy, or lower alkoxy substituted by halogen;
n is 1, 2 or 3;
m is 1, 2 or 3;
Ar is a five or six membered heteroaryl group, selected from:

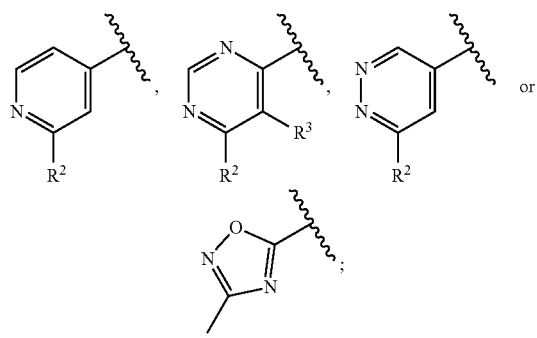

wherein:
$R^2$ is hydrogen, halogen, lower alkyl, lower alkyl substituted by halogen, or lower alkoxy;
$R^3$ is hydrogen or halogen; and
—( )$_m$— is —(CH$_2$)$_m$—;
and, optionally, converting the compound obtained into a pharmaceutically acceptable acid addition salt.

11. A compound of formula I, prepared by the process of claim 10.

12. A medicament containing one or more compounds according to claim 1, and pharmaceutically acceptable excipients.

13. A method for modulating γ secretase activity, the method comprising administering an effective amount of a compound of claim 1 to a subject in need thereof.

* * * * *